(12) United States Patent
McIntosh et al.

(10) Patent No.: US 8,967,494 B2
(45) Date of Patent: *Mar. 3, 2015

(54) FUEL INJECTOR

(75) Inventors: Andrew McIntosh, Leeds (GB); Novid Beheshti, Birmingham (GB)

(73) Assignee: University of Leeds, Leeds (GB)

( * ) Notice: Subject to any disclaimer, the term of this patent is extended or adjusted under 35 U.S.C. 154(b) by 1528 days.

This patent is subject to a terminal disclaimer.

(21) Appl. No.: 11/992,571

(22) PCT Filed: Sep. 26, 2006

(86) PCT No.: PCT/GB2006/003582
§ 371 (c)(1),
(2), (4) Date: Apr. 22, 2009

(87) PCT Pub. No.: WO2007/034230
PCT Pub. Date: Mar. 29, 2007

(65) Prior Publication Data
US 2009/0212125 A1 Aug. 27, 2009

Related U.S. Application Data

(60) Provisional application No. 60/720,716, filed on Sep. 26, 2005.

(51) Int. Cl.
*B05B 1/24* (2006.01)
(52) U.S. Cl.
USPC .......................................... 239/136; 239/135
(58) Field of Classification Search
USPC ................................ 239/136, 133, 135, 138
See application file for complete search history.

(56) References Cited

U.S. PATENT DOCUMENTS

| | | |
|---|---|---|
| 3,653,444 A | 4/1972 | Livingston |
| 3,731,876 A | 5/1973 | Showalter |
| 3,762,378 A | 10/1973 | Bitonti |
| 3,868,939 A | 3/1975 | Friese et al. |
| 4,010,748 A | 3/1977 | Dobritz |
| 4,026,285 A | 5/1977 | Jackson |
| 4,254,833 A | 3/1981 | Perry |
| 4,522,183 A | 6/1985 | Meier et al. |
| 5,449,041 A | 9/1995 | Galbraith |
| 5,645,225 A | 7/1997 | Hasegawa et al. |
| 5,678,637 A | 10/1997 | O'Connell |
| 5,865,156 A | 2/1999 | Feucht et al. |

(Continued)

FOREIGN PATENT DOCUMENTS

| | | |
|---|---|---|
| CH | 324 334 A | 9/1957 |
| CN | 1539395 A | 10/2004 |

(Continued)

OTHER PUBLICATIONS

Office Action from corresponding U.S. Appl. No. 11/528,297 dated Oct. 7, 2009.

(Continued)

*Primary Examiner* — Len Tran
*Assistant Examiner* — Viet Le
(74) *Attorney, Agent, or Firm* — Wolf, Greenfield & Sacks, P.C.

(57) ABSTRACT

A method and apparatus is disclosed for ejecting material. The ejected material is ejected as liquid and liquid vapor via an explosive process which can provide a very fast ejection as well as an ejection which has a large throw. The apparatus can be used to eject fuel for a fuel injector.

29 Claims, 21 Drawing Sheets

(56) References Cited

U.S. PATENT DOCUMENTS

| | | |
|---|---|---|
| 6,213,089 B1 | 4/2001 | Cheng |
| 6,213,104 B1 | 4/2001 | Ishikiriyama et al. |
| 6,350,116 B1 | 2/2002 | Herrmann |
| 6,543,420 B2 | 4/2003 | Kohketsu et al. |
| 6,595,208 B1 | 7/2003 | Coffee et al. |
| 7,117,867 B2 | 10/2006 | Cox et al. |
| 7,128,067 B2 | 10/2006 | Byron et al. |
| 7,975,687 B2 | 7/2011 | Grundler et al. |
| 8,100,191 B2 | 1/2012 | Beheshti et al. |
| 2002/0079377 A1 | 6/2002 | Nichols |
| 2003/0079745 A1 | 5/2003 | Bunke et al. |
| 2003/0088207 A1 | 5/2003 | Rogatchev et al. |
| 2005/0045179 A1 | 3/2005 | Faison et al. |
| 2005/0205084 A1 | 9/2005 | Gupta et al. |
| 2009/0165787 A1 | 7/2009 | Ahlmen et al. |
| 2010/0031957 A1 | 2/2010 | McIntosh et al. |
| 2010/0032176 A1 | 2/2010 | McIntosh et al. |

FOREIGN PATENT DOCUMENTS

| | | |
|---|---|---|
| DE | 296 02 969 U1 | 6/1996 |
| DE | 196 37 025 A1 | 3/1998 |
| DE | 20310436 U1 | 12/2003 |
| EP | 0816088 A1 | 1/1998 |
| EP | 0820780 A | 1/1998 |
| EP | 1061246 A2 | 12/2000 |
| EP | 1 449 596 A1 | 8/2004 |
| FR | 2 047 010 A1 | 3/1971 |
| GB | 2202440 A | 9/1988 |
| JP | 46-4691 A | 11/1971 |
| JP | S46-004691 A | 11/1971 |
| JP | 53-21323 A | 2/1978 |
| JP | S56-002864 A | 1/1981 |
| JP | S58-114759 A | 7/1983 |
| JP | S58-139099 A | 8/1983 |
| JP | 09-280123 A | 10/1997 |
| JP | H10-277442 A | 10/1998 |
| JP | 11-241657 A | 9/1999 |
| JP | 2001-118817 A | 4/2001 |
| JP | 2003-117020 A | 4/2003 |
| JP | 2003-181335 A | 7/2003 |
| JP | 2003-193944 A | 7/2003 |
| JP | 2003-232234 A | 8/2003 |
| JP | 2004-162586 A | 6/2004 |
| JP | 2004-251193 A | 9/2004 |
| JP | 2004-356285 A | 12/2004 |
| JP | 2005-502434 A | 1/2005 |
| JP | 2006501871 A | 1/2006 |
| JP | 2006-520692 A | 9/2006 |
| SU | 792 645 A1 | 12/1985 |
| WO | WO 95/14450 A2 | 6/1995 |
| WO | WO 03/024618 A1 | 3/2003 |
| WO | WO 03/059413 A2 | 7/2003 |
| WO | WO 2004/092569 A2 | 10/2004 |
| WO | WO 2004/092569 A3 | 8/2005 |
| WO | WO 2007/034226 A1 | 3/2007 |
| WO | WO 2007/034229 | 3/2007 |

OTHER PUBLICATIONS

International Preliminary Report on Patentability and Written Opinion for International Application No. PCT/GB2006/003576 dated Mar. 26, 2008.
Office Communication mailed Nov. 29, 2012 for U.S. Appl. No. 11/992,565.
Office Communication mailed Feb. 25, 2013 for U.S. Appl. No. 11/992,567.
International Preliminary Examination Report on Patentability from PCT/GB2006/003582 dated Apr. 3, 2008.
Office action from corresponding U.S. Appl. No. 11/528,297 dated Aug. 28, 2008.
Office action from corresponding U.S. Appl. No. 11/528,297 dated Mar. 5, 2009.
International Search Report and Written Opinion for International Application No. PCT/GB2006/003568 dated Dec. 18, 2006.
International Search Report and Written Opinion for International Application No. PCT/GB2006/003576 dated Dec. 27, 2006.
International Search Report and Written Opinion for International Application No. PCT/GB2006/003582 dated Feb. 13, 2007.
International Preliminary Examination Report on Patentability from PCT/GB2006/003568 dated Apr. 3, 2008.
Office Communication for U.S. Appl. No. 11/528,297 dated Mar. 24, 2010.
Notice of Allowance for U.S. Appl. No. 11/528,297 dated Jan. 11, 2011.
Notice of Allowance for U.S. Appl. No. 11/528,297 dated Sep. 22, 2011.
Office Communication mailed Jan. 5, 2011 for U.S. Appl. No. 11/992,565.
Office Communication mailed Jul. 6, 2011 for U.S. Appl. No. 11/992,565.
Office Communication mailed Apr. 3, 2012 for U.S. Appl. No. 11/992,565.
Office Communication mailed Dec. 6, 2011 for Japanese Application No. 2008-532860. 3 pages.
Office Communication mailed May 15, 2012 for Japanese Application No. 2008-532861. 3 pages.
Office Communication mailed May 27, 2014 for Japanese Application No. 2013-090505.
Office Communication issued Sep. 29, 2014 for Chinese Application No. 201210234088.4.

FUEL INJECTOR

BACKGROUND

The present invention relates to a method and apparatus for ejecting target mass. In particular, but not exclusively, the present invention provides a method and apparatus for a fast mass ejection device able to eject liquid and/or liquid vapour quickly and over relatively long distances from an ejection chamber in which a quantity of liquid is stored. Still more particularly, but again not exclusively, the present invention relates to a fuel injector and method for injecting fuel.

There is a need in a number of industries for mass ejection devices. That is to say, devices which will send out a spray of liquid and liquid vapour at a fixed or variable rate and over a desired distance. Preferably there is a need for a spray of liquid and liquid vapour to occur at a fast rate and over a great distance. In such systems the term "throw" is often referred to as a characteristic of a spray. The throw of material is defined as the distance traveled divided by the length of a chamber from which the spray is ejected.

Various examples of mass ejection devices are known such as fire extinguishers, ink jet printers, air bag igniters, fuel injectors for motor engines and gas turbines, pilot flames, etc. In each of these there are specific problems associated with the device in question, however, for each applied technology there is a continuing desire to be able to eject liquid and liquid vapour quickly and over a large distance.

By way of example of a problem specific to an application of mass ejection systems, reference is made to a gas turbine reigniter. In the igniter of a gas turbine, the conventional approach to reignite gas in a combustion chamber is to pass a current between two electrodes of a reigniter and create for a short while a mixture of electrically charged radicals. This is illustrated more clearly in FIG. 1 in which a conventional reigniter 10 is shown including an outer electrode 11 which is generally cylindrical in shape with an internally located pellet 12. A central electrode 13 is located within the pellet and by passing a current between the two electrodes 11, 13 a mixture of electrically charged radicals (that is when the gas molecules split temporarily into charged components referred to as a plasma). This plasma only lasts for a fraction of a second before recombining and losing its charge. The charge is then used to ignite combustion in a main combustion chamber of the main engine. A problem with such known reigniters is in getting the mixture to be ejected as ejected material via the exit orifice 14 far enough and to remain charged long enough to perform its objective function. The ejected material 15 has been used to ignite the kerosene or other usual gas turbine engine fuel.

By way of a further example of a problem specific to an application of mass ejection systems, reference is made to a fuel injector. Prior art fuel injectors use electro-mechanical nozzles and a pre-pressurised fuel to produce a finely atomised spray. Fuel is pressurised within a chamber and an electromagnetic coil lifts a needle of its seal so fuel can squeeze through the nozzle's aperture through an intake valve. Control of the timings of the release of this pressurised liquid is controlled by electronics. This has the disadvantage of costly and complex materials which are prone to error and require many working parts.

A further example of a use of a mass ejector system is in a pilot flame for furnace and boilers used in the energy industry or land based gas turbines.

SUMMARY OF THE INVENTION

It is an aim of the present invention to at least mitigate the above-mentioned problems.

It is an aim of embodiments of the present invention to provide an apparatus and method for providing a fuel injector.

It is an aim of embodiments of the present invention to provide an apparatus and method for ejecting material whereby liquid and liquid vapour are ejected from a chamber, the ejected material having desirable characteristics such as speed of ejection and distance traveled by the ejected material.

It is an aim of embodiments of the present invention to provide an apparatus and method for providing a fast mass ejector.

It is an aim of embodiments of the present invention to provide an apparatus and a method for providing a pilot flame igniter.

It is an aim of embodiments of the present invention to provide an apparatus and a method for providing a propulsion unit which may be used to propel vehicles.

It is an aim of embodiments of the present invention to provide an apparatus and method for providing a fire extinguisher.

According to a first aspect of the present invention there is provided apparatus for injecting fuel into a combustion zone, comprising:

an ejection chamber to hold a portion of a selected liquid fuel;

an inlet valve arranged to selectively open to transfer liquid into the ejection chamber; and an exit valve arranged to selectively open to eject fuel from said ejection chamber when a parameter associated with said ejection chamber satisfies a predetermined condition; wherein liquid and/or liquid vapour are ejected from the ejection chamber into the combustion zone via the exit valve thereby injecting fuel into the combustion zone.

According to a second aspect of the present invention there is provided apparatus for injecting fuel into a combustion zone, comprising:

an ejection chamber to hold a portion of a selected liquid fuel;

an inlet valve arranged to selectively open to transfer liquid into the ejection chamber; and an exit valve arranged to selectively open to eject fuel from said ejection chamber when a parameter associated with said ejection chamber satisfies a predetermined condition, said exit valve further being arranged to open when a temperature of liquid in the ejection chamber is equal to or greater than a saturation temperature associated with the liquid at a pressure equal to a pressure of gas located downstream of said exit valve; wherein liquid and/or liquid vapour are ejected from the ejection chamber into the combustion zone via the exit valve thereby injecting fuel into the combustion zone.

According to a third aspect of the present invention there is provided a method for injecting fuel into a combustion zone, comprising the steps of:

providing an ejection chamber for holding a portion of a selected liquid fuel;

selectively opening an inlet valve to transfer a portion of liquid into the ejection chamber;

selectively opening an exit valve of said ejection chamber when a parameter associated with said ejection chamber satisfies a predetermined condition; and ejecting liquid vapour and/or liquid from the ejection chamber into the combustion zone via the exit valve.

According to a fourth aspect of the present invention, there is provided an apparatus for ejecting material, comprising;

a chamber for holding a body of a selected liquid;

an inlet valve via which the selected liquid can be introduced into the chamber;

an exit valve arranged to open to allow contents from the chamber to be ejected when a parameter satisfies a predetermined condition; and means that increases pressure of the liquid in the chamber; wherein liquid and/or liquid vapour are ejected from the chamber via the exit valve.

Preferably said means for increasing pressure comprises a heating element arranged to heat the body of liquid located in the chamber.

Preferably said exit valve is arranged to open when the pressure within the chamber reaches a predetermined value.

Preferably said inlet valve is arranged to open to allow liquid to be introduced into the chamber subsequent to the contents of the chamber previously being ejected via the opening of the exit valve.

Preferably said chamber further comprises a narrow neck region along which liquid and vapour is ejected.

Preferably the liquid and vapour are ejected via a vapour explosion process when the exit valve opens.

Preferably said liquid is water.

Preferably said liquid is a flammable liquid, for example kerosene or petrol.

Preferably said exit valve is set to open at 1.1 bar pressure.

Preferably said means for increasing pressure comprises means for heating the liquid above its boiling point at atmospheric pressure.

Preferably said chamber diameter is in the range of 1 mm to 1 meter.

Preferably said chamber is spherical in shape.

Preferably said chamber is heart-shaped.

Preferably said exit valve is located at an apex region of said heart-shaped chamber.

Preferably said chamber is substantially cylindrical in shape.

According to a fifth aspect of the present invention, there is provided a method for ejecting material from a chamber, comprising the steps of:

introducing a selected liquid into the chamber via an inlet valve;

increasing pressure of the liquid in the chamber;

opening an exit valve when a parameter satisfies a predetermined condition; and ejecting liquid and/or liquid vapour from the chamber via the exit valve.

Preferably the method further comprises the steps of heating liquid located in the chamber via a heating element previous to the step of opening the exit valve.

Preferably the method further comprises the steps of determining when a predetermined parameter is satisfied and opening the exit valve responsive thereto.

Preferably the method further comprises the steps of heating the liquid in the chamber to a temperature above its boiling temperature at the pressure of gas located at a downstream position from the exit valve.

According to a sixth aspect of the present invention there is provided an apparatus for injecting fuel into a downstream combustion zone, comprising:

an ejection chamber to hold a body of a selected liquid which is to be injected;

an inlet valve via which the selected liquid can be introduced into the chamber;

an exit valve arranged to open to allow contents of the chamber to be ejected when a parameter satisfies a predetermined condition; and means that increases pressure in the chamber; wherein liquid and/or liquid vapour are ejected via the exit valve.

Preferably the liquid and liquid vapour are ejected via a vapour explosion process.

Preferably the liquid and liquid vapour are ejected as a spray having a throw greater than 20.

Preferably said liquid and liquid vapour are ejected as a spray having a throw greater than 100.

Preferably said liquid comprises kerosene.

Preferably said liquid comprises petrol.

Preferably said chamber is manufactured from a metallic material.

Preferably said means for increasing pressure comprises a heating element located within the chamber.

Preferably the apparatus further comprises a power source for the heating element.

Preferably said chamber is substantially cylindrical in shape and has a neck region at an exit end, the exit valve being located in the neck region.

Preferably said neck region includes a narrow ejection orifice via which liquid fuel and liquid fuel vapour is ejected into the combustion zone.

Preferably a cross section of the orifice has a diameter less than a cross section of the neck region.

Preferably the apparatus further comprises an ignition source located in the combustion zone for igniting the liquid fuel and liquid fuel vapour ejected into the combustion zone via the injecting apparatus.

According to a seventh aspect of the present invention there is provided a method for injecting fuel into a downstream combustion zone, comprising the steps of:

introducing a selected liquid into the chamber via an inlet valve;

increasing pressure of the liquid in the chamber;

opening an exit valve when a parameter satisfies a predetermined condition; and ejecting liquid and liquid vapour from the chamber via the exit valve.

Preferably the method further comprises the steps of:

heating liquid located in the chamber via a heating element previous to the step of opening the exit valve.

According to an eighth aspect of the present invention there is provided an apparatus for providing propulsion to a vehicle, comprising:

a fuel ejection chamber to hold a body of a selected liquid fuel;

an inlet valve via which a selected liquid can be introduced into the ejection chamber;

an exit valve arranged to open to allow contents from the ejection chamber to be ejected when a parameter satisfies a predetermined condition;

means for increasing pressure of the liquid in the ejection chamber; and a combustion chamber located so as to receive liquid and liquid vapour ejected from said ejection chamber and including an igniter element for igniting the liquid and/or liquid vapour ejected from the ejection chamber.

Preferably said combustion chamber further comprises an outlet through which flame and hot gases may escape from the combustion chamber, the escape of the flame and hot gases providing an urging force in an opposite direction for a vehicle.

Preferably said ignition element comprises a spark igniter.

Preferably an ejected material directing nozzle is directed in a downstream location with respect to said exit valve for directing liquid and liquid vapour ejected from the ejection chamber in a desired direction.

Preferably the apparatus further comprising at least one air intake for providing air in said combustion chamber.

Preferably said at least one air intake comprises one or more air breathing passages drawing air from an exterior of a vehicle into the propulsion system.

Preferably said vehicle comprises an unmanned aerial vehicle (UAV).

Preferably said means for increasing pressure comprises a heating element arranged to heat the body of liquid located in the ejection chamber.

Preferably said exit valve is arranged to open when the pressure within the ejection chamber reaches a predetermined value.

According to a ninth aspect of the present invention there is provided a method for providing propulsion for a vehicle, comprising the steps of:
  introducing a selected liquid fuel into an ejection chamber of said vehicle via an inlet valve;
  increasing pressure of the liquid in the ejection chamber;
  opening an exit valve when a parameter satisfies a predetermined condition;
  ejecting liquid and liquid vapour from the ejection chamber via the exit valve;
  igniting the ejected liquid and/or liquid vapour together with air in a combustion chamber located so as to receive the ejected liquid and liquid vapour from the ejection chamber; and
  directing flame and hot gases resulting from the combustion process out from the combustion chamber in a first direction so as to provide propulsion for the vehicle in a direction substantially opposite to the first direction.

Preferably the method further comprises the steps of:
  igniting a mixture of the ejected liquid and liquid vapour together with air via an ignition element located in the combustion chamber.

Preferably the method further comprises the steps of directing the ejected liquid and liquid vapour from the ejection chamber in a desired direction in the combustion chamber via a nozzle element located at a downstream location from said exit valve.

Preferably the method further comprises the steps of providing air into said combustion chamber via at least one air intake.

Preferably the further comprises the steps of heating liquid located in the ejection chamber via a heating element previous to the step of opening said exit valve.

Preferably the present invention provides a vehicle comprising the apparatus.

Preferably said vehicle is an unmanned aerial vehicle (UAV).

According to a tenth aspect of the present invention there is provided an apparatus for extinguishing a fire, comprising:
  an ejection chamber to hold a body of a selected extinguishing liquid;
  an inlet valve via which the selected liquid can be introduced into the ejection chamber;
  an exit valve arranged to open to allow material in the chamber to be ejected when a parameter satisfies a predetermined condition; and
  means that increases pressure in the chamber; wherein extinguishing liquid and/or extinguishing liquid vapour are ejected via the exit valve.

Preferably the liquid and liquid vapour are ejected via a vapour explosion process.

Preferably the liquid and liquid vapour are ejected as a spray having a throw greater than 20.

Preferably said liquid and liquid vapour are ejected as a spray having a throw greater than 100.

Preferably said liquid comprises water.

Preferably the apparatus further comprises a liquid reservoir for providing extinguishing liquid to said ejection chamber via said inlet valve.

Preferably said reservoir is portable and said apparatus further comprises a handle for holding said liquid reservoir.

Preferably said liquid reservoir is connected to said chamber via a pipework arrangement, said pipework arrangement being connected to further chambers each arranged to eject extinguishing liquid and liquid vapour via a respective exit valve.

Preferably said chamber has a capacity of 100 ml.

According to an eleventh aspect of the present invention there is provided a method for fighting fires, comprising the steps of:
  introducing a fire extinguishing liquid into a chamber via an inlet valve;
  increasing pressure of the liquid in the chamber;
  opening an exit valve when a parameter satisfies a predetermined condition; and
  ejecting extinguishing liquid and liquid vapour from the chamber via the exit valve, said ejected liquid and/or liquid vapour being directed at said fire to thereby extinguish the fire.

Preferably the method further comprises the steps of heating liquid located in the chamber via a heating element previous to the step of opening the exit valve.

Preferably the method further comprises the steps of determining if a predetermined condition indicating the existence of a fire is satisfied; and
  ejecting liquid and liquid vapour from said chamber responsive to a result of said determination step.

Preferably the method further comprises the steps of a user carrying a liquid reservoir to which said chamber is secured to a location where the existence of a fire has been identified.

Preferably the method further comprises the steps of automatically ejecting liquid and liquid vapour from said exit valve when the existence of a fire is identified.

According to a twelfth aspect of the present invention there is provided an apparatus for providing a pilot flame igniter, comprising:
  an ejection chamber to hold a body of a selected flammable liquid;
  an inlet valve via which the selected liquid can be introduced into the chamber;
  an exit valve arranged to open to allow contents of the chamber to be ejected when a parameter satisfies a predetermined condition; and
  means that increases pressure in the chamber; wherein liquid and/or liquid vapour are ejected via the exit valve.

Preferably the liquid and liquid vapour are ejected via a vapour explosion process.

Preferably said selected liquid comprises a liquid fuel such as kerosene and/or petrol.

Preferably the apparatus having a dead time between consecutive ejections less than a time taken to burn the liquid and liquid vapour ejected via the exit valve during a single exit valve opening operation.

Preferably said ejection chamber has an internal capacity predetermined so as to provide a short down time for said pilot flame igniter.

Preferably the apparatus further comprises a pump arranged to pump liquid fuel into the chamber via said inlet valve.

According to a thirteenth aspect of the present invention there is provided an apparatus for reigniting fuel in a combustion chamber of a gas turbine, comprising:

an ejection chamber to hold a body of a selected liquid which is to be injected into the combustion chamber;
an inlet valve via which the selected liquid can be introduced into the ejection chamber;
an exit valve arranged to open to allow contents of the ejection chamber to be ejected when a parameter satisfies a predetermined condition; and
means for increasing pressure in the chamber; wherein
liquid and/or liquid vapour are ejected via the exit valve into the combustion chamber.

Preferably said gas turbine reigniter apparatus is arranged to eject liquid and liquid vapour via a vapour explosion process.

Preferably the apparatus further comprises a plurality of said apparatus disposed within a combustion chamber of a gas turbine.

Preferably the apparatus further comprises a plurality of fuel injectors disposed to inject fuel into the combustion chamber.

According to a fourteenth aspect of the present invention there is provided a method for reigniting fuel in a combustion chamber of a gas turbine, comprising the steps of:

storing a selected liquid in an ejection chamber;
increasing pressure in the ejection chamber; and
ejecting liquid and/or liquid vapour via an exit valve into the combustion chamber, said ejected material reigniting fuel in the combustion chamber.

Preferably the method further comprises the steps of timing the ejection of liquid and liquid vapour from the ejection chamber to coincide with a predetermined point in a cycle of a fuel injector arranged to inject fuel into the combustion chamber.

Preferably said selected liquid comprises a liquid fuel such as petrol or kerosene.

Preferably the method further comprises the step of ejecting liquid and liquid vapour into the combustion chamber via a vapour explosion process.

According to a fifteenth aspect of the present invention there is provided an apparatus for delivering a medicament to a patient, comprising:

an ejection chamber arranged to hold a body of a selected liquid including at least one medicament component;
an exit valve arranged to open to allow contents of the chamber to be ejected when a predetermined parameter is satisfied;
means that increases pressure in the chamber; and
means that locates an exit orifice of said apparatus at a desired location; wherein
liquid and/or liquid vapour are ejected from the chamber at the desired location to thereby deliver medicament to that location.

Preferably the apparatus further comprises a means for determining where said apparatus is located in said patient.

Preferably said selected liquid comprises a liquid medicament.

Preferably said selected liquid comprises a carrier liquid with a drug in solution.

Preferably the apparatus further comprises a flexible shaft having a distal end locatable at a target location.

Preferably the apparatus further comprises a camera.

Preferably the apparatus further comprises a light source.

Preferably the apparatus further comprises a body portion arranged to be located in a tube-like body portion and to move down the tube-like portion responsive to a bodily process.

Preferably the apparatus further comprises a wireless communication link receiver to receive a wireless signal when said apparatus is at a desired location.

Preferably the apparatus further comprises means for opening said exit valve response to receipt of said wireless signal.

According to a sixteenth aspect of the present invention there is provided a method for delivering a medicament to a patient, further comprising the steps of:

storing a selected liquid including at least one medicament component in an ejection chamber;
locating an exit orifice of said chamber at a desired location;
increasing pressure in the chamber;
opening an exit valve to allow contents of the chamber to be ejected via the exit orifice when a parameter satisfies a predetermined condition; and
ejecting liquid and/or liquid vapour at the desired location to thereby deliver medicament at that location.

According to a seventeenth aspect of the present invention there is provided an apparatus for clearing a blockage of a tubular element in a patient, comprising:

an ejection chamber arranged to hold a body of a selected liquid;
an exit valve arranged to allow contents of the chamber to be ejected when a parameter satisfies a predetermined condition;
means that increases pressure in the chamber; and
means that locates an exit orifice of said apparatus at a desired location; wherein
liquid and/or liquid vapour are ejected from the chamber at the desired location to thereby clear the blockage.

Preferably the liquid and liquid vapour are ejected in a substantially axial direction with said tubular element.

Preferably the exit orifice of said apparatus is movable with respect to a remainder of the apparatus.

Preferably said tubular element comprises an artery or vein of said patient.

According to a eighteenth aspect of the present invention there is provided a method for clearing a blockage of a tubular element in a patient, comprising the steps of:

holding a body of a selected liquid in an ejection chamber;
locating an exit orifice of said chamber at a desired location in said patient;
increasing the pressure in the chamber, and
via an exit valve, allowing contents of the chamber to be ejected when a parameter satisfies a predetermined condition; wherein
liquid and/or liquid vapour are ejected from the chamber to thereby clear a blockage of the tubular element in the patient.

Embodiments of the present invention provide an ejection chamber in which liquid and liquid vapour are exploded from an exit orifice. The vapour explosion has the effect that target material is blasted out from the ejection chamber very rapidly and over distances not previously obtainable with known techniques.

Using a vapour explosion gives a longer throw than classical fuel injectors. For example, the throw of a liquid and liquid vapour explosion in accordance with embodiments of the present invention may be around 200 to 300 times or more its corresponding chamber length. For a classical fuel injector similar values would be of the order of 10 to 20 times an injection chamber size. This is because of the dynamics of the vapour explosion which occurs as a large pressure of liquid in an ejection chamber is cyclically built up and then released.

Embodiments of the present invention can provide a fuel ignition system in which the vapour explosion chamber used to eject material can be used to inject fuel (used as its liquid) into a combustion chamber. The injected fuel is mostly vaporized (around 70% or more of ejected mass is fuel vapour) before exiting the injector nozzle. This is of a significant benefit because any liquid fuel has first to be vaporized to be able to react with air (oxygen). With known fuel injectors, liquid fuel must first be atomised to enhance its vaporization. This step is not required according to embodiments of the present invention since the injector according to an embodiment of the present invention injects readily vaporized or already vaporized fuel. This significantly facilitates the ignition and combustion processes.

Embodiments of the present invention used as fuel injectors also provide the advantage that the new injector requires much lower pressures to inject an amount of fuel relative to known injectors injecting that same amount of fuel. For example, in prior art petrol engines which operate at much lower pressures than diesel ones, the injection pressure is about 100 bars. Embodiments of the present invention provide a fuel injector which requires pressures of only 10 to 15 bars. This makes the system cheaper to make and to maintain.

Embodiments of the present invention provide a fuel injector having a longer throw than known prior art fuel injectors. This has the advantage of having a more rapid and better mixing and vaporization of the fuel.

Embodiments of the present invention provide a gas turbine reigniter which is able to reignite fuel in a combustion chamber of a gas turbine more quickly and in a more controlled manner than is possible with previously known techniques.

Embodiments of the present invention provide a pilot flame igniter able to ignite target fuel very quickly and over a great distance relative to the size of the igniter apparatus and amount of fuel used. By repeatedly ejecting fuel from the ejection chamber the pilot igniter can be kept alight.

Embodiments of the present invention provide a propulsion unit which can be used for vehicles. The propulsion unit can be small scale and even nano scale and much lighter than known propulsion units since the ejection used to propel a vehicle is very powerful, fast and occurs energetically over a great distance.

Embodiments of the present invention provide a fire extinguisher system which can either be portable or fixed, for use internally in buildings or vehicles, which, once triggered, can operate very rapidly to eject fire suppressant material at the heart of a fire. The use of spray has been found to be beneficial when fighting fires.

BRIEF DESCRIPTION OF THE DRAWINGS

Embodiments of the present invention will now be described hereinafter, by way of example only, with reference to the accompanying drawings in which.

DETAILED DESCRIPTION

Figure 1:
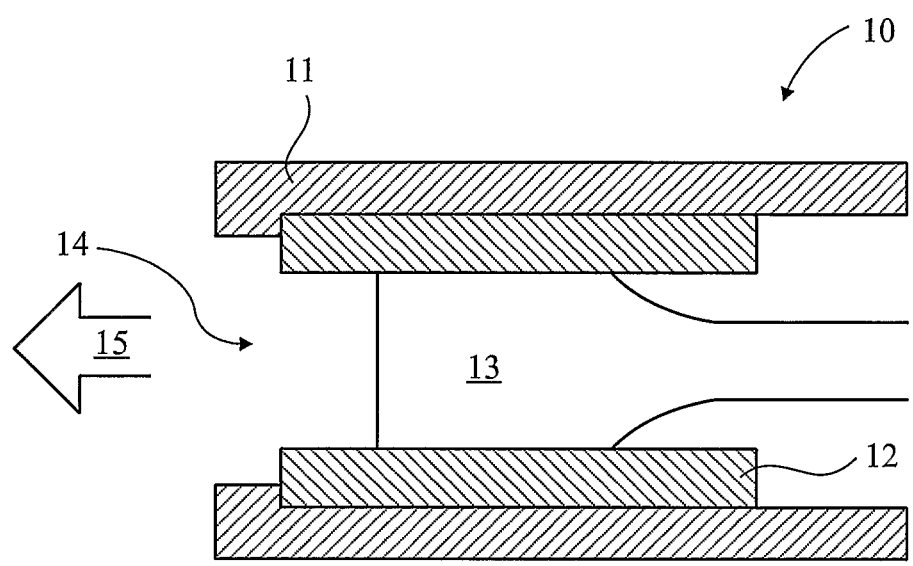
FIG. 1 illustrates a prior art gas turbine reigniter.

In the drawings like reference numerals refer to like parts.

FIG. 2 illustrates an ejection system 20 for ejecting liquid and liquid vapour via a vapour explosion process in accordance with an embodiment of the present invention. An ejection chamber 21 is formed in a generally cylindrical shape from a material such as steel or other rigid material which is able to withstand substantial pressure and temperature changes. It will be understood that embodiments of the present invention are not limited to combustion chambers having this specific shape, nor indeed to combustion chambers formed from steel. At a first end region of the chamber 21, signified by reference numeral 22, an inlet valve 23 is located so as to allow a selected liquid such as water to enter the central region 24 of the chamber via an associated inlet pipe 25. At a further end region 26 of the chamber 21 is located an exit valve 27 which opens to allow material to be ejected from the chamber region 24 through a nozzle region 28.

A heating element 29 is provided by an electric heater located in the ejection chamber. The electric heater is connected to a power source (not shown) so that when turned on the heater operates to heat up a body of liquid located in the region 24 of the chamber. It will be understood that according to further embodiments of the present invention (some of which are described hereinbelow) other ways of raising the pressure and temperature of liquid in the ejection chamber may be provided.

Figure 2A:
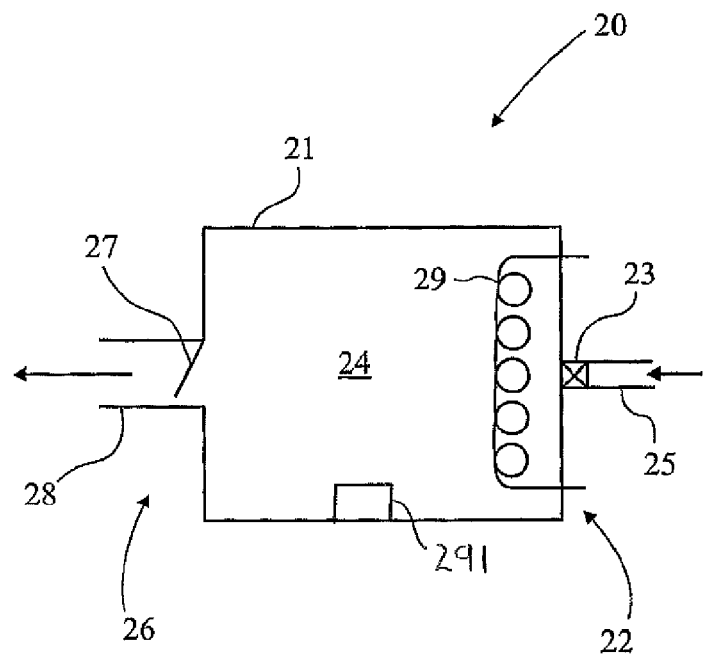
FIGS. 2a and 2b illustrate apparatus for ejecting material.
Figure 2B:
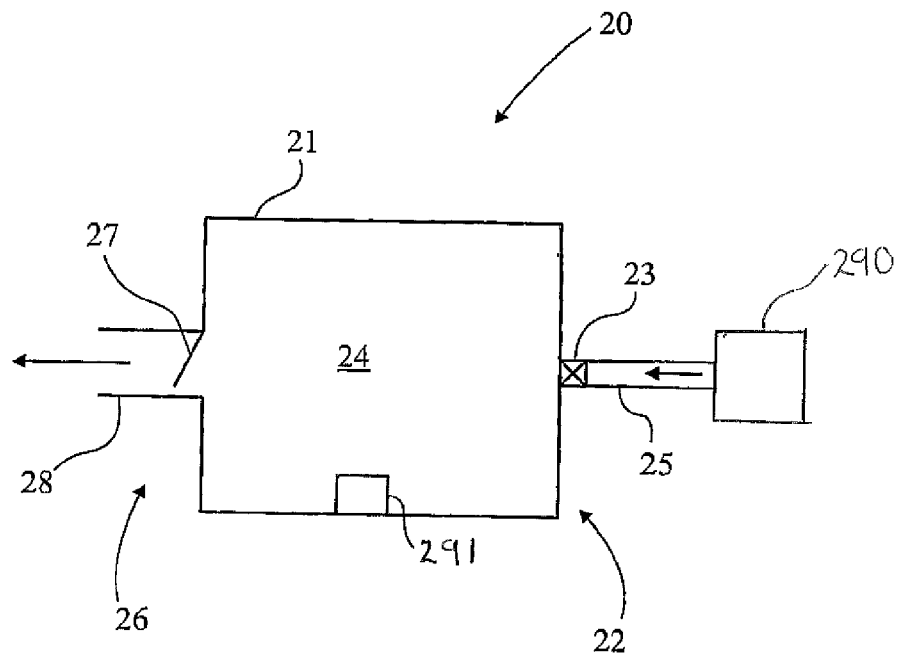

As shown in FIG. 2a, the pressure of a liquid in the central region 24 of the chamber may be increased by heating the liquid in it. Prior to this stage the exit valve 27 is closed to prevent outgress of liquid. The inlet valve 23 is opened to allow liquid water to enter the chamber until the chamber is full or contains a predetermined quantity of liquid. The inlet valve is then closed sealing the body of liquid thereby located in the chamber. The heater element then operates to heat the liquid. As a result of this the liquid expands due to thermal expansion raising the pressure of the liquid inside the chamber. Whilst the heating can be done by heating elements, it would of course be possible to have a preheated liquid supply at the inlet to the chamber under high pressure as shown in FIG. 2b. If this technique is adopted the pressure rise in the chamber is performed by a pump 290 which is feeding the liquid supply into the chamber through the inlet valve. By heating the water the pressure in the chamber therefore rises. Also, the temperature rises. The exit valve is controlled so that the valve "blows" so as to open at a predefined/predetermined pressure. The pressure can be monitored by one or more pressure sensors 291 such as pressure transducers located in the chamber or close to the chamber. The water or other liquid in the chamber is thus heated by an electrical element (much like an electric kettle) and then rises to a boiling temperature well above its boiling temperature at atmospheric pressure. The boiling point represents a saturation point and it will be appreciated that this is determined by the relationship between pressure and temperature of the particular liquid used. It is advantageous that the liquid in the ejection chamber is close to, equal to or above its saturation point at a pressure which is the pressure downstream of the exit valve of the chamber. The temperature raises above the boiling temperature at atmospheric pressure because the water is kept in the chamber by both an inlet valve which closes prior to the water being heated and an exit valve which only allows a release once the system has reached a particular pressure. At this pressure and temperature, which may be referred to as a trigger pressure and trigger temperature respectively, the valve blows in a similar way to a pressure cooker. A vapour explosion then takes place which causes a combination of liquid and liquid vapour (if the liquid is water the liquid vapour would be steam) to exit from the chamber. When the exit valve opens the steam and water mixture is ejected via the opening 28.

When the exit valve opens initially a first phase to be ejected is a liquid phase in the form of shattered liquid in a spray. This ejection occurs in a matter of microseconds subsequent to the exit valve opening. This extremely rapid ejection of liquid has particular advantages. A few microseconds later a mixture of liquid and liquid vapour is ejected. Some microseconds later a mixture containing slightly less liquid and more vapour is ejected.

However this initial liquid discharge can be altered or totally removed when higher trigger temperatures for the same ambient pressure are used. On the other hand lowering the trigger temperature can lead to situations where practically only atomised liquid is ejected. In this way the proportion of liquid and vapour can be selected by varying one or more parameters associated with the ejection chamber. Selectively varying one or more parameters such as temperature or pressure can also be used to selectively control drop size in the ejected material.

As material is ejected from the ejection chamber, the pressure drops. When the pressure has dropped back to an ambient or second predetermined pressure, which may be referred to as the closure pressure, the exit valve is closed and the inlet valve opened again to introduce new liquid material into the chamber. This restarts the cycle. Consequently a repeated cycle of steam/water mixture or other liquid/liquid vapour is exhausted from the outlet once sufficient pressure is generated by heating up the new supply of liquid water.

The size of the chamber can vary and may, for example, be less than a centimeter in diameter. For example, the chamber may even be at the nano size to mm diameter. Alternatively, the chamber may be a meter or more in diameter. It will be appreciated that as the size of the chamber increases, the frequency of the blasts will reduce since the time taken to increase the pressure will increase appropriately. It will be understood that as the size of the chamber is increased according to specific uses, larger pumps and/or valves will be required.

Preferably the inlet valves can be controlled to maximise the proportion of liquid ejected from the chamber. This can be achieved by selecting the diameter of the inlet port to be almost equal, or equal to that of the exit or exhaust port, this should ensure that too much liquid does not get into the chamber.

Figure 3:
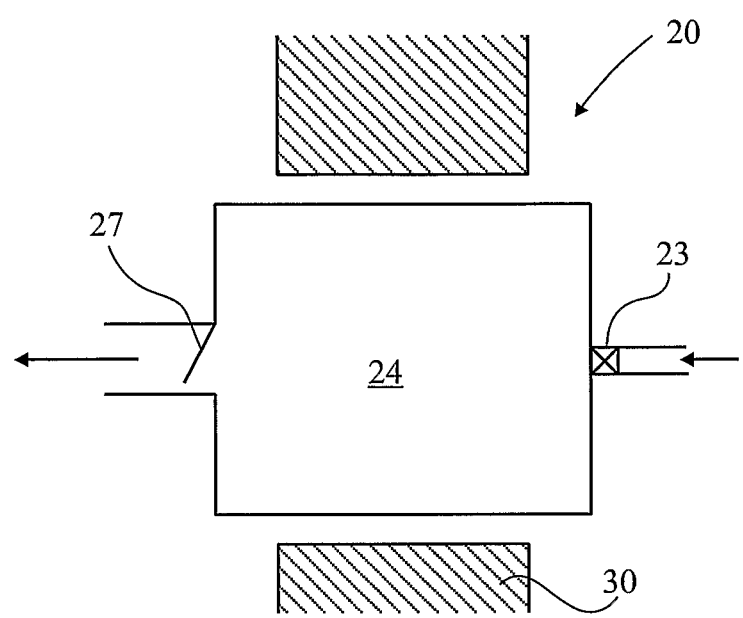
FIG. 3 illustrates an alternative embodiment of apparatus for ejecting material.

FIG. 3 illustrates an alternative embodiment of the ejection apparatus which shares many features in common with the embodiments shown in FIG. 2. The embodiment of the present invention illustrated in FIG. 3 uses a heat exchanger 30 which encloses a side wall portion of the chamber to heat liquid in the chamber. This manner of heating liquid is particularly advantageous when the liquid ejected is not water but is a fuel which is subsequently burned. The generation of this heat at a location downstream of the exit valve can be used to heat the heat exchangers and thus heat the liquid in the chamber.

Figure 4:
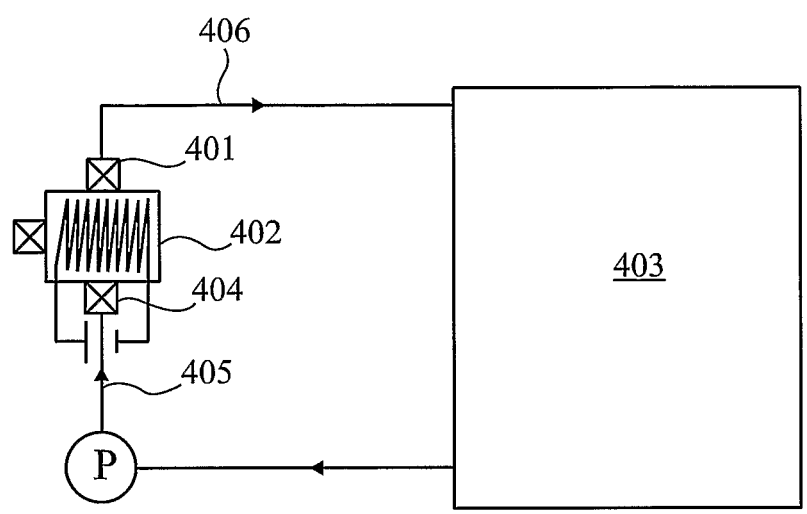
FIG. 4 illustrates a further alternative embodiment of apparatus for ejecting material.

To enable faster refilling of liquid in the chamber, a return port and valve can be added to the chamber as shown in FIG. 4. The return port and valve 401 allow for some of the liquid and vapour in the chamber 402 to return to the reservoir 403 when the inlet valve 404 is opened for replenishment. The addition of the return port and valve 401 should help enable sufficient fresh liquid to be added to the chamber 402 to compensate for the ejected mass and therefore avoid lack of liquid in the chamber 402 after consecutive ejections. In the case of usage of pipelines (such as with fire fighting sprinklers) as a reservoir the return port 406 connected to the return valve 401 may be connected to a different pipeline at a lower pressure than the supply pipeline 403 and preferably be at ambient pressure.

In an embodiment of the present invention a chamber can be used having an internal diameter of 25 mm and a length of 32 mm. Two or more separate heaters could be inserted into the chamber. The first, a helical coil located near the walls of the chamber with length of 28 mm, external diameter of 21 mm, internal diameter of 15 mm and power of 500 W. The second, a cartridge heater located near the centre of the chamber with length of 25 mm, diameter of 1 cm and power of 200 W. With these specifications, repetitive steam/water spray ejections of up to 5 Hz is possible. Higher frequencies would lead to a pure liquid un-atomised jet since the cold water fed to the chamber for refill after each blast does not have enough time to be heated by this heat power to above the boiling point. The reservoir can therefore be kept at a higher temperature, for example about 75° C. to shorten the heat up in the chamber between ejections, and consequently allowing for an increase in the frequency of ejections.

Figures 5A, 5B:
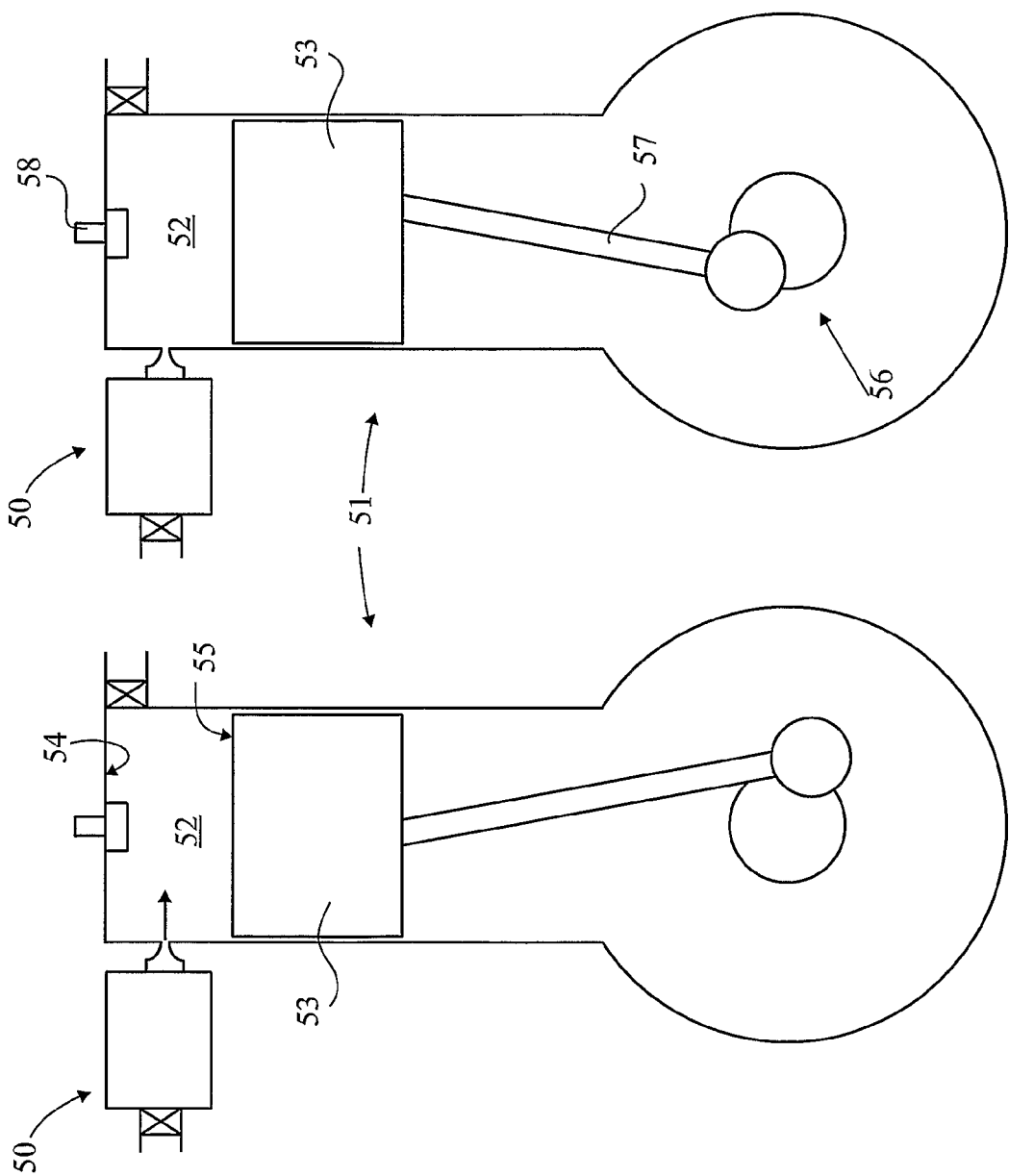
FIG. 5 illustrates a combustion engine incorporating an embodiment of the present invention.

FIG. 5 illustrates the use of a further embodiment of the present invention as a fuel injector unit 50. A combustion engine 51 is illustrated in an intake stage (shown in FIG. 5A) and an exhaust phase (illustrated in FIG. 5B). The combustion engine includes a cylindrical combustion chamber 52 closed at a first end by a tight-fitting piston 53 which is arranged to slide within the chamber. The movement of the piston varies the volume in the chamber 52 between the closed end of the chamber 54 and a combustion surface 55 of the piston. An opposed side of the piston connects to a crank shaft 56 via a piston rod 57. The crank shaft transforms the reciprocating motion of the piston into rotary motion.

The combustion engine illustrated in FIG. 5 is a four stroke internal combustion engine, however, it will be understood that embodiments of the present invention are not restricted to use of fuel injectors with such types of engine. Rather a four stroke internal combustion engine is referred to here by way of example only. On the first downward stroke of the piston, fuel is injected via the fuel ejector 50 into the combustion chamber 52.

Prior art fuel injectors use electro-mechanical nozzles and a pre-pressurised fuel to produce a finely atomised spray. Fuel is pressurised within a chamber and an electromagnetic coil lifts a needle of its seal so fuel can squeeze through the nozzle's aperture through an intake valve. Control of the timings of the release of this pressurised liquid is controlled by electronics. This has the disadvantage of costly and complex materials which are prone to error and require many working parts. Embodiments of the present invention overcome this by replacing the known fuel injector systems with an ejection chamber 50 which ejects liquid fuel and liquid fuel vapour into the combustion chamber 52 via a vapour explosion process as noted above. The vaporized fuel and liquid fuel is ignited via an ignition element such as a spark plug 58.

Figure 6:
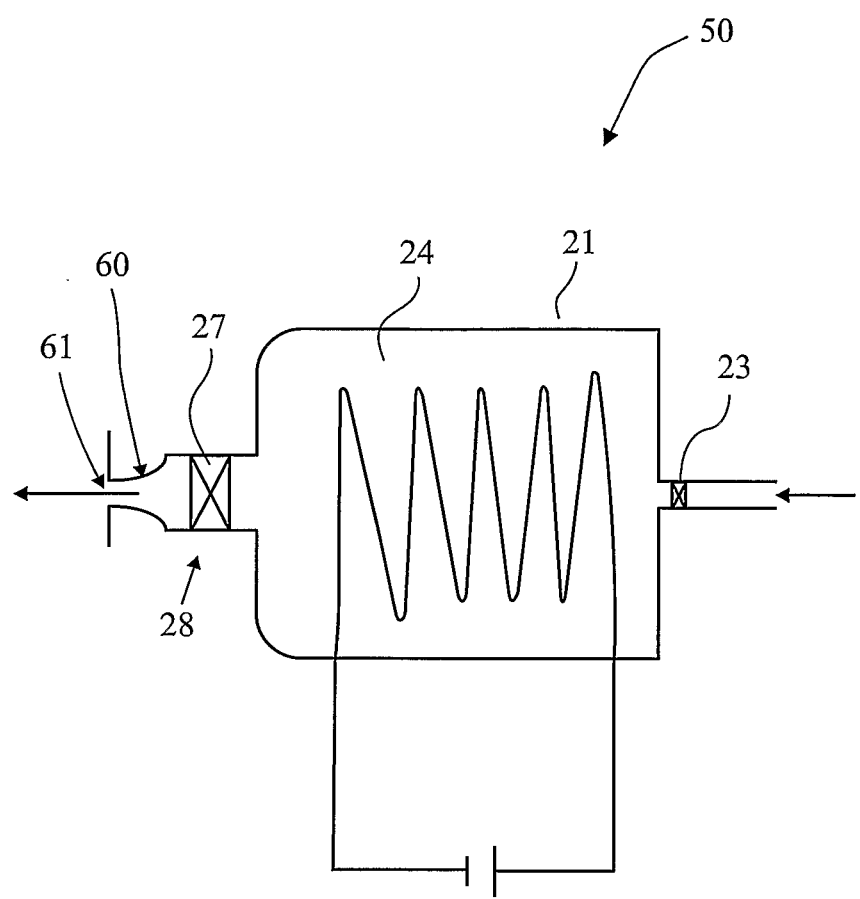
FIG. 6 illustrates a fuel injector.

A fuel injector system in accordance with an embodiment of the present invention is shown in more detail in FIG. 6. The fuel injector 50 comprises an ejection chamber 21 defining a space 24 within which liquid fuel can be input via an inlet valve 23. A return port and valve may be incorporated within this embodiment of the present invention thus enabling for faster refilling of liquid within the chamber. It will be understood that such a return port and valve could be used in any embodiment described herein. A heating element 29 is used to heat a body of liquid located inside the ejection chamber subsequent to its introduction through the inlet valve. An exit valve 27 constrains the liquid within the chamber until a predetermined pressure is reached. This pressure is greater than atmospheric pressure or the pressure experienced by ejected material downstream (that is to say to the left-hand side shown in FIG. 6). In this way liquid in the chamber can be heated above the boiling point temperature which will be experienced when the exit valve is opened. When the exit valve is thus opened the pressure will drop thus causing the liquid in the ejection chamber to boil rapidly and in an explosive manner due to its elevated temperature above its natural boiling point. It will be noted that for certain fluids, for example, for kerosene and gasoline, the fluids are themselves multi-component fuels which include different hydrocarbons. Each of these has a different boiling point. For gasoline, for example, the boiling points range from 117° C. (for the most volatile component) to 200° C. for the heaviest component and for kerosene the boiling points range from 150° C. to 300° C. In order to have optimum performance it is preferable that the temperature should be kept above the higher boiling point to make sure that all components are going to vaporize. This is, of course, not necessary. For example, where one knows which component has the dominant concentration, then that component's boiling point may be used to fix the temperature ensuring that the rest of the fuel will boil. It will be appreciated that at higher temperatures for the same given pressure the spray will be finer and a proportion of vapour of the ejected material will be greater. It will be appreciated that the temperatures given here are examples of the corresponding boiling (saturation) points at atmospheric pressure. These will be very different at elevated pressures and reference may be made to known databases of thermophysical properties of materials to obtain working pressures. A nozzle 60 provides a narrowing of a neck region 28 and ejected liquid and liquid vapour are ejected through an opening 61 into the combustion chamber 52 of the combustion engine.

The heat required to bring the fuel to the designated temperature can be partially or totally obtained from the heat produced by the engine. Since the injector can be located within or near the combustion-chamber of the engine which when in operation will be very hot, the vapour explosion chamber can be designed in a way that it absorbs as much heat as is needed from the engine. This heat or thermal energy can be obtained through the chamber walls of the injector, through a heat exchanger going into the chamber, or a combination of the two techniques. Additionally, the inlet fuel pipe can go through, or be adjacent to, the hot parts of the engine body to heat up the fuel nearer to the designated temperature. However, it is preferable to keep this temperature below the saturation temperature of the lightest component of the fuel to avoid unfavourable cavitations in the pipeline.

An advantage of applying the above-described vapour explosion technology to fuel injection systems is to greatly enhance the throw of the devices and consequently the response of the engines to an increased power output. For an average sized family car, according to known prior art techniques, a normal operating range is 2,000-6,000 rpm with a Formula I car attaining perhaps 17,000 rpm. In accordance with embodiments of the present invention, a time taken for one cycle of a fuel injector which comprises a short ejection phase, followed by a longer refilling and repressurising phase, can be around 5 milliseconds or less. The rate of fuel injection is thus around 12,000 injections per minute. In a common four stroke engine there are typically two revolutions per injection and therefore 24,000 rpm could, in theory, be achieved. In order to avoid disintegration of the engine, some form of limiting constraint may therefore be utilised to slow down the ejection process. The process of ejecting fuel from the chamber of the injector can be controlled by selecting a parameter or multiple parameters of the ejection process, such as the period of time that the exhaust valve is open for, the temperature and pressure of the fuel injection chamber, and the pressure of the combustion chamber of the engine. It will be appreciated that other parameters may be controlled to provide desired results.

Further advantages of applying the vapour explosion technology for the purpose of fuel injection include:
1. A considerable fraction of the fuel spray volume will be taken by the fuel vapour immediately after emerging from the nozzle. This promotes the ignition and burning rate of fuel and thus provides higher acceleration of the engine.
2. The fuel spray can easily have smaller drop sizes in comparison to most conventional atomisers. This enhances ignition and burning velocity which in turn enhance the acceleration of the engine. Smaller droplets also lead to more complete combustion, fewer amounts of pollutants and better fuel economy.
3. Use of vapour explosion can greatly enhance the 'throw' of these devices, and consequently the response of the engines to an increased power output.
4. Work can be carried out at much lower pressures than conventional atomisers since a high fraction of the volume inside the nozzle is fuel vapour and due to vapours lower density lower pressures can be used to make the fuel move at the same ejection velocities. These lower pressure ejections are practically achieved by making use of the high ratio of thermal energy to mechanical energy in atomising the liquid. This in turn can enhance the engine efficiency since the thermal energy in most cases is readily available from the combustion itself and is usually taken away as a loss by the cooling system and this could have lower energy losses compared to purely mechanical energy usage.
5. Very wide angles for the spray can be utilised even with very simple nozzle designs, such as plain orifices. Wide angle spray is very favourable in most combustion systems as it can give better mixing with air and higher burning rates.
6. The pressure build-up in the atomiser can be produced either solely by the thermal expansion of the fuel or by a combination of this with the supply pressure of a fuel pump. Thus, even less mechanical energy is needed.

Figure 7:
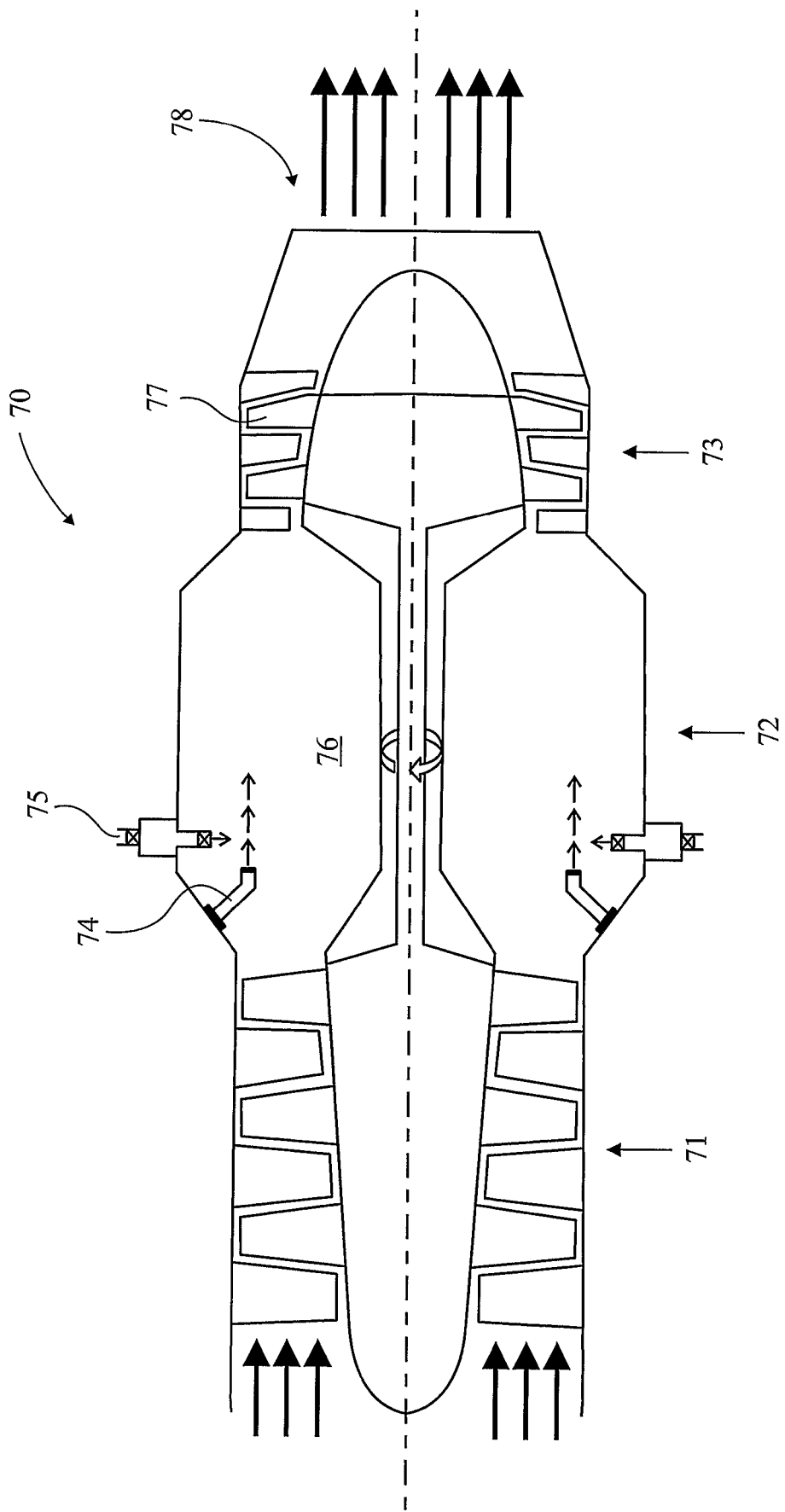
FIG. 7 illustrates a gas turbine.

FIG. 7 illustrates how an embodiment of the present invention may be applied to provide a gas turbine reigniter. FIG. 7 illustrates a gas turbine 70 comprising three main sections. These are the compressor 71, combustor 72 and turbine 73.

Outside air is drawn into the engine by the action of the compressor. The air is mechanically compressed by the motion of the compressor blades consequently the pressure and temperature of the air increases with the corresponding decrease in volume. The mechanical energy used to compress the air is thus converted into kinetic energy in the form of compressed air. The compressed air is then forced through into the combustion section into which fuel is injected via a fuel injector 74. The fuel injector may be of a conventional type or may be of a type previously described hereinabove. A fuel reigniter 75, in accordance with an embodiment of the present invention, is then used to ignite the fuel converting the chemical energy into thermal energy in the form of hot expanding gas. Fuel is repeatedly injected into the combustion section to ensure continuous combustion. Rather than repeated injection, fuel may be constantly injected. Volume of gas and temperature increase while the pressure remains substantially constant through the combustor chamber 66. The hot expanding gas's thermal energy is converted to mechanical energy as the turbine 73 is rotated by virtue of the gas acting on fins 77 of the turbines. Hot exhaust gas then exits out via a front end 78 of the gas turbine. The output turbine is connected to the compressor blade thus helping to power the compression of air.

As noted above, known reignition devices (for example as shown in FIG. 1) include complex plasma arrangements to reignite material in the combustion chambers 76 of gas turbines. It will be appreciated that the combustion chamber may contain many fuel injectors distributed throughout the chamber in an advantageous manner and one or more fuel reigniters may be provided to reignite fuel injected by each of the injectors. Alternatively, it will be understood that the locations of the fuel injectors may be carefully designed so that less than one reigniter is required per injector. Gas turbines have many applications such as jet engines in the aerospace/nautical industries, engines for land vehicles, as well as electrical power generation using land based gas turbines. Some land based gas turbines can use igniter technology to help the turbine run at low Nitrogen Oxide (NOx) conditions, This helps stability of combustion within the turbine.

Figure 8:
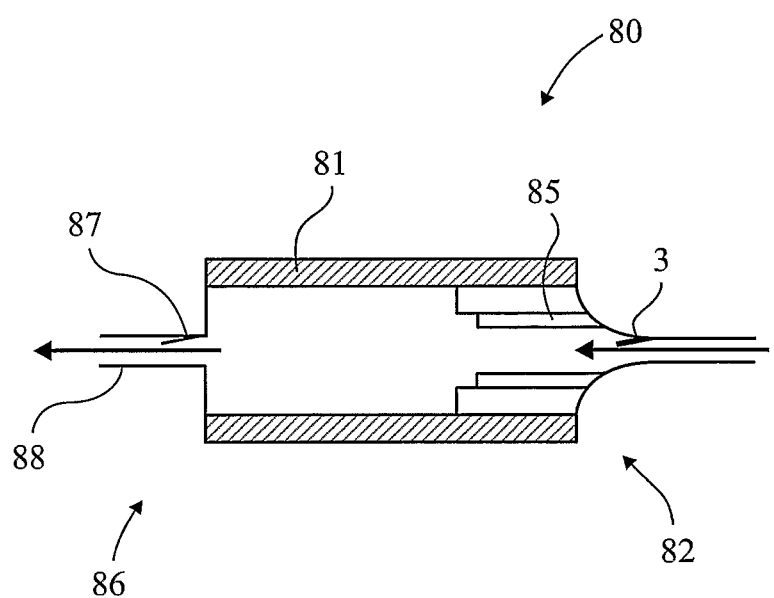
FIG. 8 illustrates a gas turbine reigniter.

FIG. 8 illustrates a gas turbine reigniter 80 in more detail. An outer electrode 81 which is substantially cylindrical in shape forms a side wall for an ejection chamber. At a first end region 82 an inlet of liquid fuel enters via an inlet valve 83. Input fuel enters a central chamber region 84. The input fuel flows through a hole in an inner electrode 85. It is worth noting that as with other embodiments hereindescribed a return port and valve could be incorporated within this embodiment of the present invention to enable faster refilling of liquid to the chamber. At a further end 86 of the ejection chamber, an exit valve 87 is located which prevents outgress of the input liquid fuel. When the exit valve 87 is opened liquid and liquid vapour are ejected via a noble 88. A central semi-conductor pellet separates the outer and inner electrodes. This element 89 is used to create charged particles to heat the liquid fuel in the chamber. As one or more pressure sensors detect the pressure in the chamber reaching a predetermined value, a current is passed through.

The reignition device of the present invention is advantageous over conventional reignition devices as a long flame is produced as a short sharp burst rather than a short flame produced continually, the latter being wasteful and less effective. Furthermore, the very fine drops and the high fuel vapour content in the spray makes it easier to ignite and keep the flame on.

Figure 9:
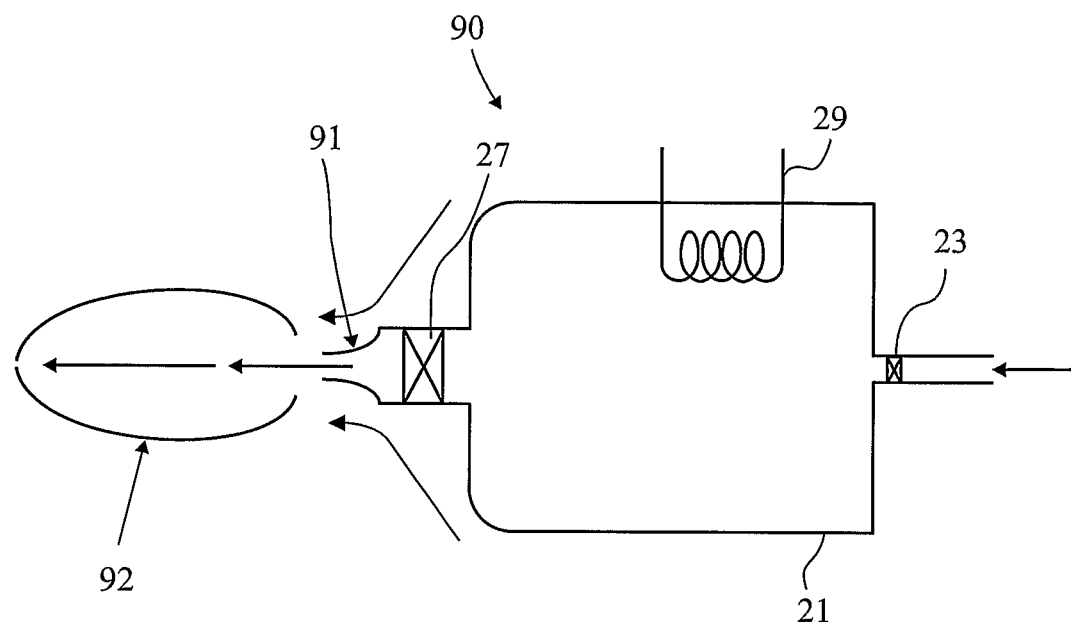
FIG. 9 illustrates a pilot igniter.

FIG. 9 illustrates an application of the vapour explosion technology in accordance with a further embodiment of the present invention in which a pilot flame igniter is provided. In this sense FIG. 9 illustrates a pilot flame ignition ejection system 90. Flame ignition systems are required for many applications such as in boilers or furnaces or domestic appliances, or domestic gas applications. Prior art ignition systems generally consist of an electronic circuit that produces a spark which consequently lights the fuel. The pilot flame igniter 90 includes a fuel chamber for storing a body of liquid introduced through an inlet valve 23. A heating element such as electric heater 29 heats the fluid as above-described which is allowed to exit the exit valve 27 when a predetermined threshold pressure is reached within the chamber. Liquid fuel and liquid fuel vapour is ejected through a nozzle 91 repeatedly as repeated vapour explosion processes take place rapidly. By virtue of the vapour explosion the fuel vapour and liquid fuel is discharged with a large throw, that is to say, over a large distance away from the nozzle 91. This may be ignited initially by an ignition element (not shown) so that a flame 92 is constantly provided to light further ignitable material. It will be appreciated that the ejection system 90 for the pilot flame provides a repeating ejection process. During an initial stage immediately after opening of the exit valve, ejected material is substantially in the form of a shattered liquid. Subsequent to this, by some tens of microseconds, the ejected material is a mix of liquid and liquid vapour. Still later the ejected material is predominantly vapour. When the exit valve closes so as to allow recharging of the ejection chamber the flame will be unanchored. The dead time caused by the closing of the exit valve is selected so as to be long enough to enable refueling of the ejection chamber but not so long that the flame burns all fuel and dies. The result will be a pilot igniter having a flame which may perceptively dance up and down but which will not be extinguished.

Figure 10:
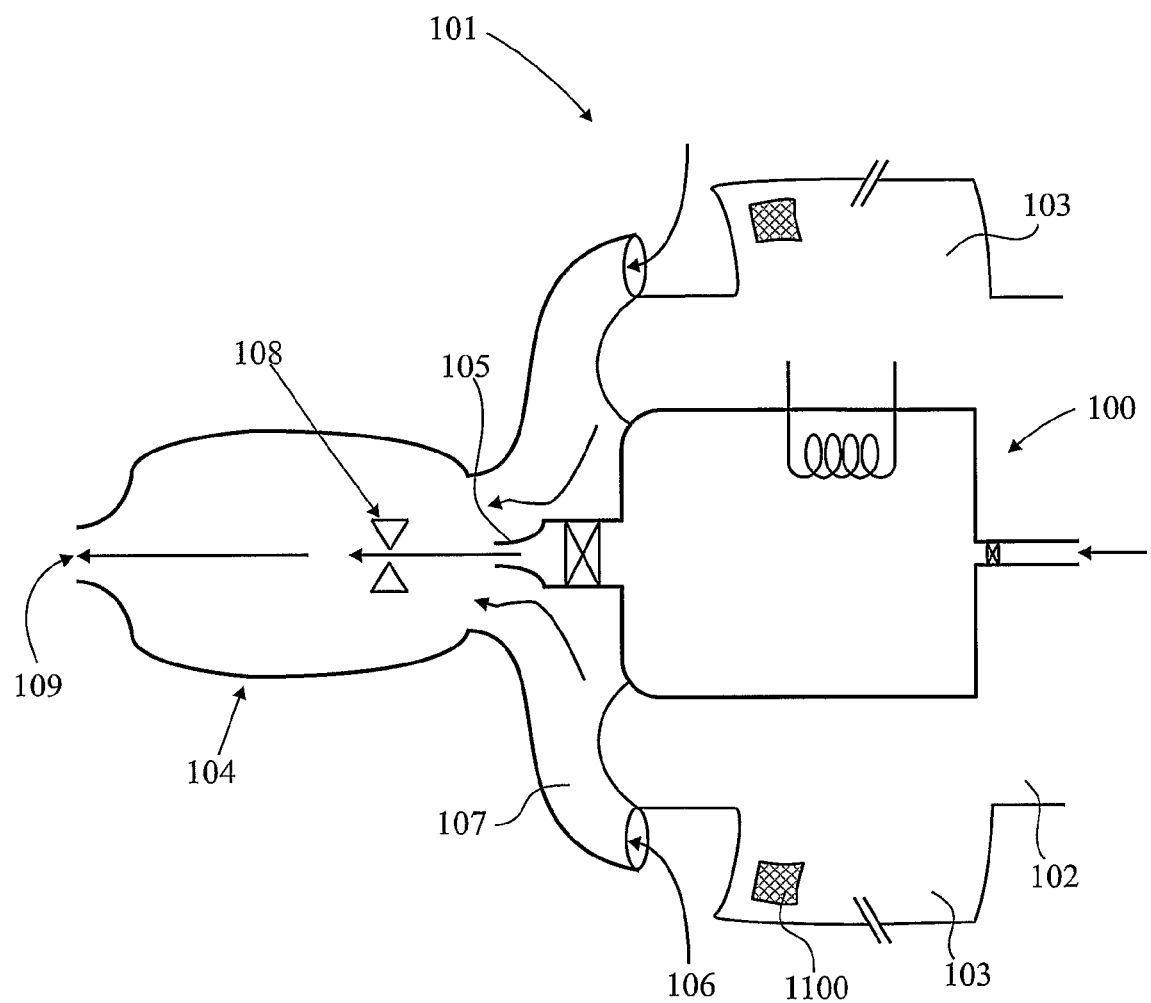
FIG. 10 illustrates a propulsion system for a vehicle.

FIG. 10 illustrates a further embodiment of the present invention in which an ejection chamber 10 is used to propel a vehicle 10. The vehicle 10 is shown as an unmanned aerial vehicle (UAV). Such vehicles are remotely piloted or self-piloted aircrafts that can carry cameras, sensors, communications equipment or other loads. It will be appreciated that embodiments of the present invention can be used to propel other types of vehicle. The UAV includes a vehicle body 10 which includes two wing sections 10 which provide lift for the vehicle. Propulsion is provided by burning liquid fuel and fuel vapour ejected from the ejection chamber system 10 in a combustion chamber 10. There are many types of UAV. Some are the size of a small plane and fly at high altitudes capable of recording and relaying large amounts of information back to a base station. Some vehicles are light enough to be carried by a single human and launched by hand. Micro air vehicles are those vehicles defined as having no dimension larger than 15 cms (6 inches). Embodiments of the present invention are also applicable to micro air vehicles or smaller.

The mass ejection chamber 10 ejects liquid fuel and liquid fuel vapour from a nozzle 10 as described hereinabove. Air is drawn into an air intake 96 and passes down inlet passages 10 where the air mixes with the fuel which is ignited by an ignition element 10, such as a spark igniter. The combustion chamber 10 constrains the combustion process and includes at least one exit orifice 10 through which burnt combustion gases and flame can escape. Propulsion is achieved by the expanding hot exhaust gases. The vapour explosion chamber 10 is of a small size so that the overall dimension of the device may be of the order of 5-10 cms in length.

Solar panels 1100 are provided to provide an energy source for the heating element and control of the igniter element 10 if required. Alternatively, an onboard light weight battery may provide the power source. As a further alternative, continuous heat exchange from the exhaust gases can provide the energy to heat inlet fuel.

Figure 11A:
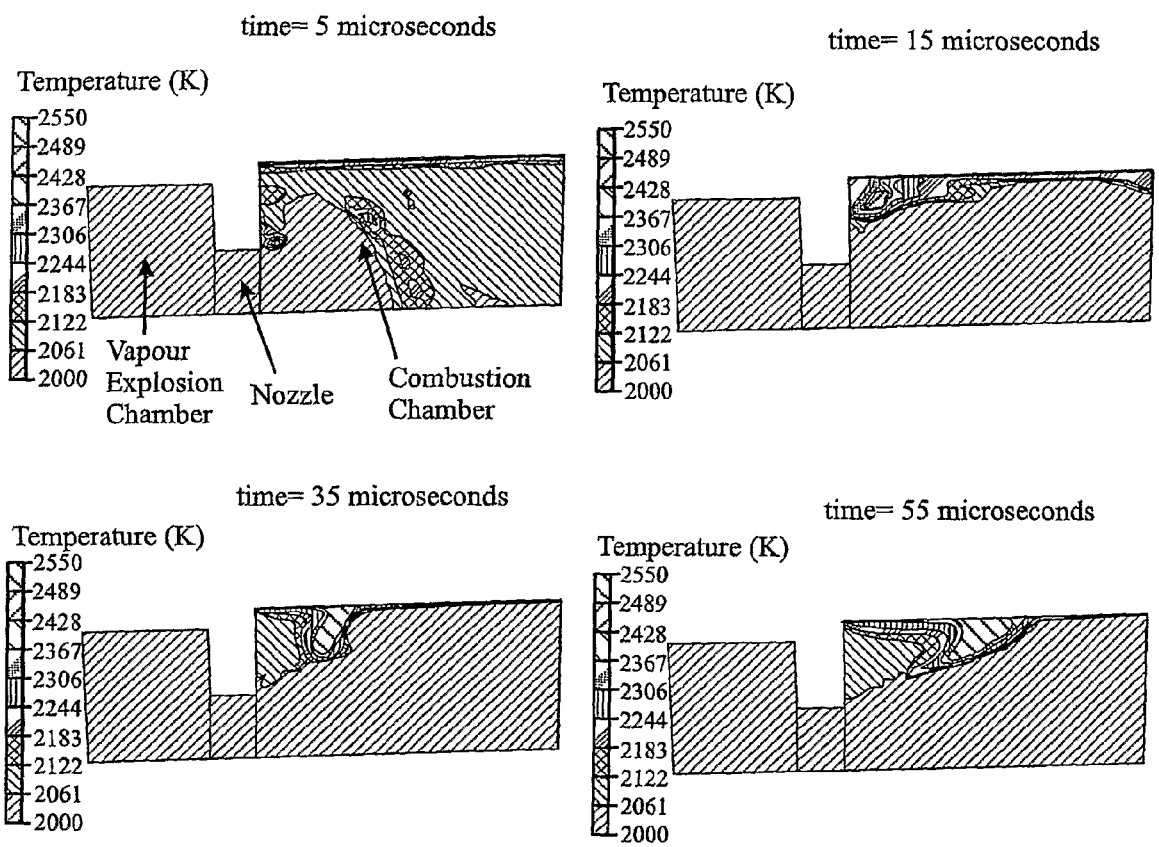
FIG. 11 illustrates combustion in a combustion chamber.
Figure 11B:
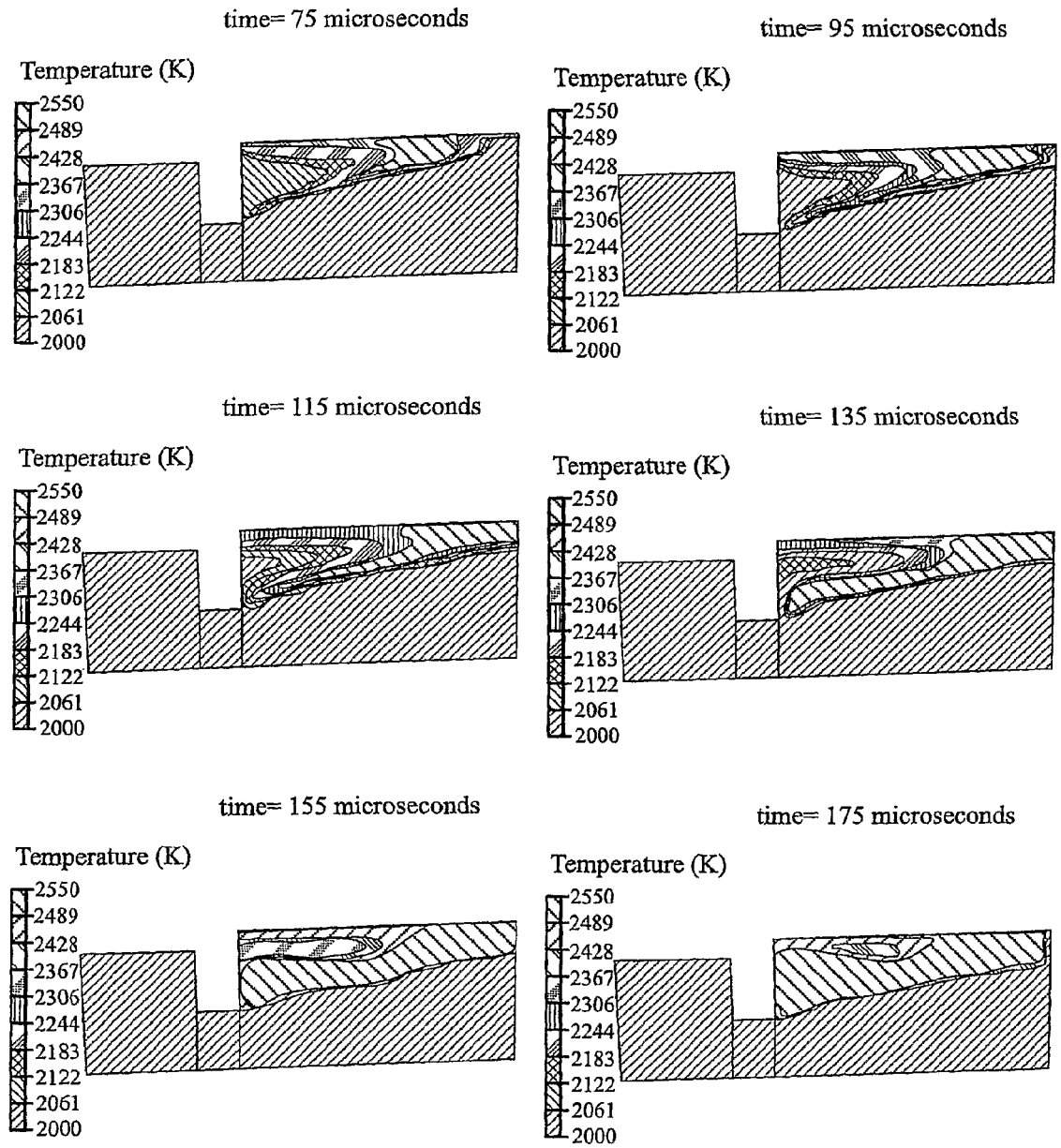
Figure 12:
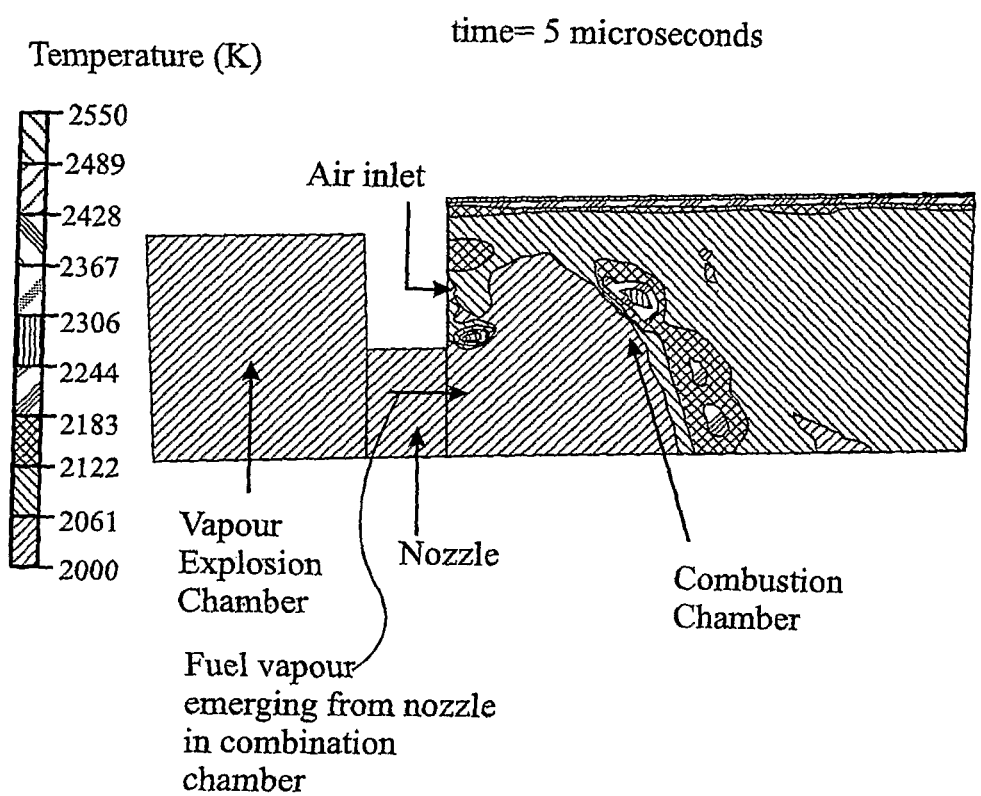
FIG. 12 illustrates an air inlet.

FIG. 11 illustrates a cycle in the vapour explosion chamber as shown in FIG. 10. In this example the vapour explosion chamber 10 and combustion chamber are 330 microns and 370 microns in diameter and 300 microns and 700 microns in length respectively. A hydrocarbon liquid fuel is vaporized in the vapour explosion chamber and the vapour is ejected from the chamber through a nozzle to the combustion chamber where it mixes with air. The air is introduced through a further inlet as shown more clearly in FIG. 12. Via an ignition device, which may be heat or flame from a preceding cycle (as shown) or a separate igniter element such as a spark igniter, the combustion is triggered and within some microseconds a flame is filling the combustion chamber. In these figures the colour/shade contours of temperature are given at different times showing the development of a flame and corresponding temperature changes over time. Since the pressure relief exit valve has to be dosed for some milliseconds between each cycle for fuel replenishment in order to keep a stable flame in the combustion chamber, it is preferable to use more than one and most preferably between 3 and 10 vapour explosion devices to eject fuel into the combustion chamber. The vapour explosion devices are positioned in a way that they inject at an identical or close to identical point in space and in the same direction but having equal or otherwise selected time delays with respect to each other in the beginning of their injection times.

Figure 13:
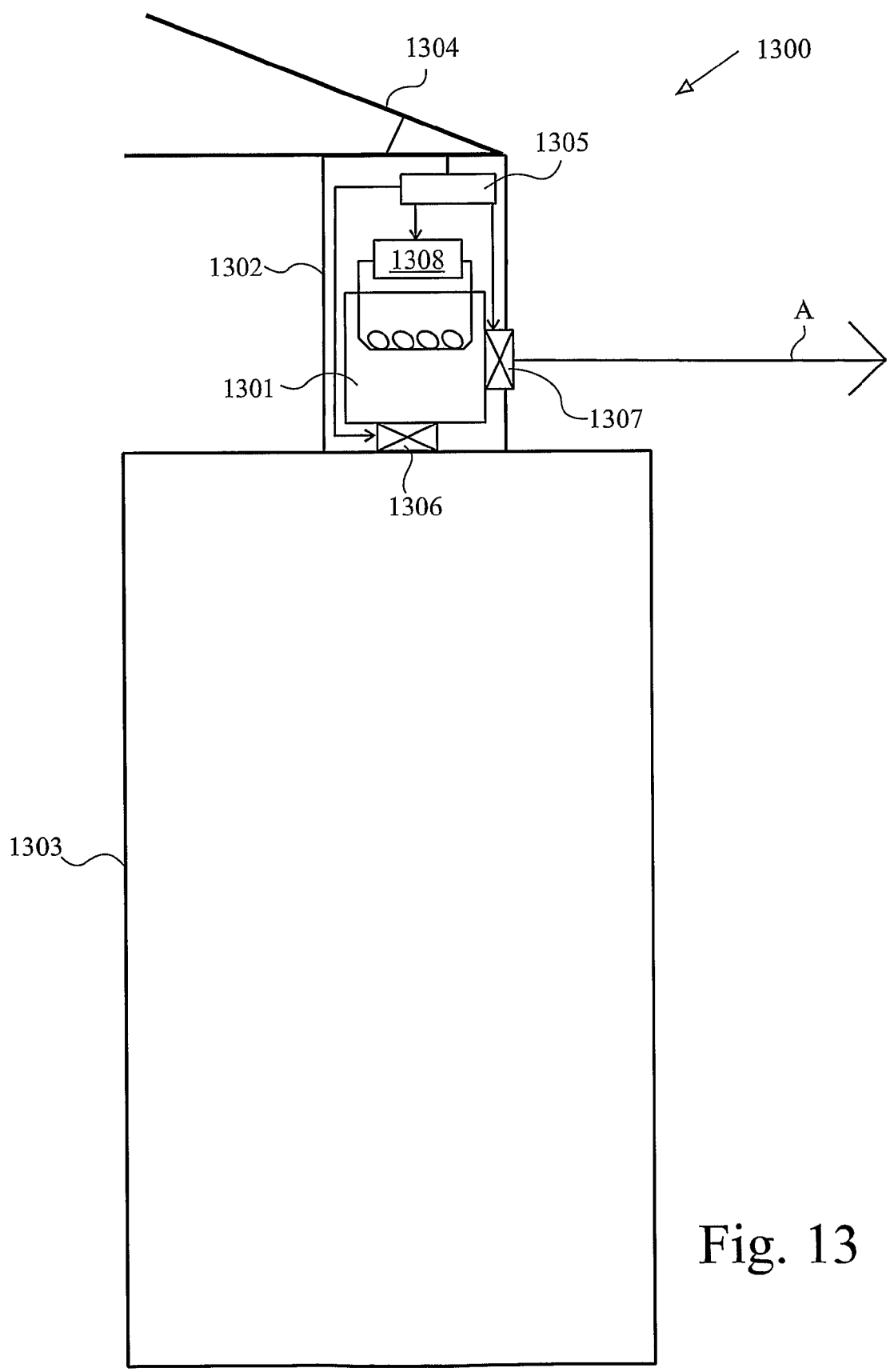
FIG. 13 illustrates a hand held fire extinguisher.

FIG. 13 illustrates an ejection system 1300 for ejecting fire suppressing liquid and fire suppressing liquid vapour via a vapour explosion process in accordance with a further embodiment of the present invention. An ejection chamber 1301 is formed in a neck region 1302 of the fire extinguisher 1300. A fluid reservoir 1303 contains a large quantity of liquid fuel suppressant such as water. A handle 1304 is used to activate the fire extinguisher by a user when the existence of a fire is determined. Activation of the handle initiates a control unit 1305 to produce drive units for controlling opening and closing of an inlet valve 1306 and outlet valve 1307. A return port and valve could also be incorporated within this system to enable faster refilling of liquid to the chamber. Liquid and liquid vapour are ejected from the chamber 1301 in the direction shown by arrow A in FIG. 13. Drive signals from the control box 1305 are also used to control a power source 1308 which controls an electric heater in the chamber 1301. The heater can be used to increase the pressure of liquid in the ejection chamber 1301 as described hereinabove. The liquid reservoir 1303 is also pressurised so that liquid is rapidly replenished in the chamber. The pressure can be so great as to increase the pressure of the liquid in the ejection chamber above atmospheric pressure.

Figure 14:
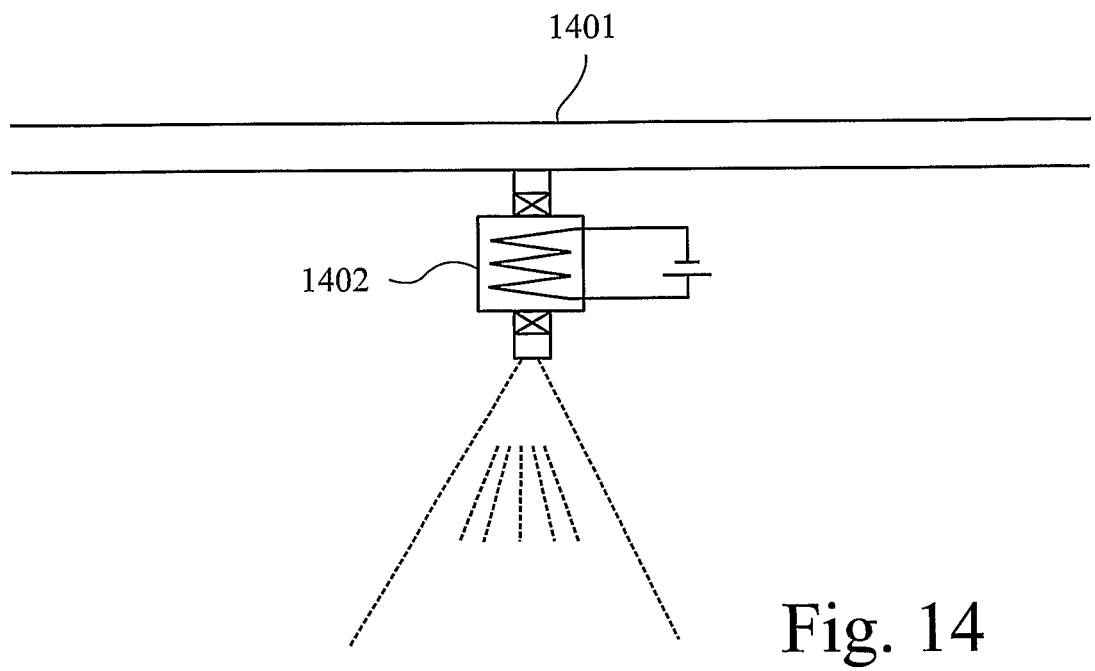
FIG. 14 illustrates a sprinkler type fire extinguisher.
Figure 15:
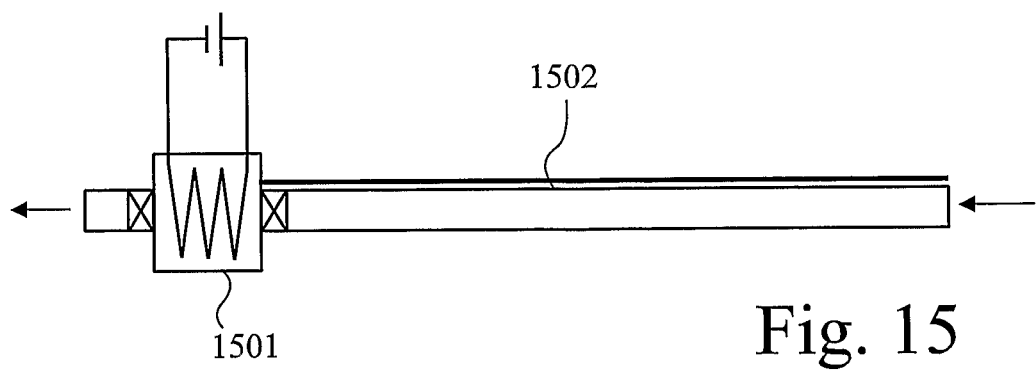
FIG. 15 illustrates a hose type fire extinguisher.

FIG. 14 and FIG. 15 illustrate two further embodiments of the present invention in which the vapour explosion device is used for ejecting fire suppressing liquid and fire suppressing vapour. FIG. 14 shows a vapour explosion device embodied as a steam sprinkler type fire extinguisher. In practice one or more vapour explosion device based fire suppressing/extinguishing sprinklers are fixed within a building and triggered by a fire detection system. A central fire detection system may be used for all sprinklers in the building or each sprinkler could have an individual sensor to allow fire suppressant to only be released at the location at which the fire is present. The system may be zoned. When a fire is detected and the extinguishing liquid is water, the sprinklers eject steam and a mist of water droplets into the environment in repetitive pulses at a specific predetermined frequency value; this could be between 0.5-5 Hz or even higher depending upon the design and specific application. As shown in FIG. 14, a sprinkler consists of a reservoir 1401, a vapour explosion chamber 1402 in accordance with the chambers outlined previously, and optionally a small pump to apply pressure to the fire suppressing liquid to help the chambers refill quickly enough for the required frequency of blasts. A single reservoir could connect to all or a specific group of sprinklers within the environment in which the sprinkler or sprinklers are located. Furthermore, such a reservoir could be a pressurised water pipe possibly alleviating the need for a pump for each sprinkler.

FIG. 15 shows a system for ejecting fire suppressing liquid. In this embodiment the vapour explosion device is used within a hose type extinguisher. The vapour explosion chamber 1501 is fitted at the tip of a hose pipe 1502. The hose pipe 1502 acts as a pressured reservoir, and provides the fire suppressing liquid to the vapour explosion chamber 1501 which blasts steam out repetitively. Power can be supplied to the vapour explosion device either by a battery attached to the vapour explosion device or a power line connection which may be attached along the hose in parallel.

In all three embodiments of the present invention which are disclosed as a system for ejecting fire suppressing liquid, the fire suppressing liquid may be water or it may be any other suitable liquid for suppressing fire.

The vapour explosion device can be advantageous in many ways over conventional water based fire suppressing devices. Firstly, vapour has a much larger surface area than the equivalent amount of water, vapour is therefore able to absorb much more heat and therefore suppress the fire better. Furthermore the vapour may engulf the fire like a mist, restricting oxygen flow to the fire and therefore suppressing the fire further. In contrast water would flow straight over the fire, only restricting oxygen flow for a very short period of time. A further advantage is that suppressing or extinguishing a fire with water vapour produced by the vapour explosion device rather than water requires the use of far less water. Using less water is not just advantageous economically and environmentally but it also means that the process of extinguishing a fire will cause less damage to the environment in which the fire has broken out.

Figure 16:
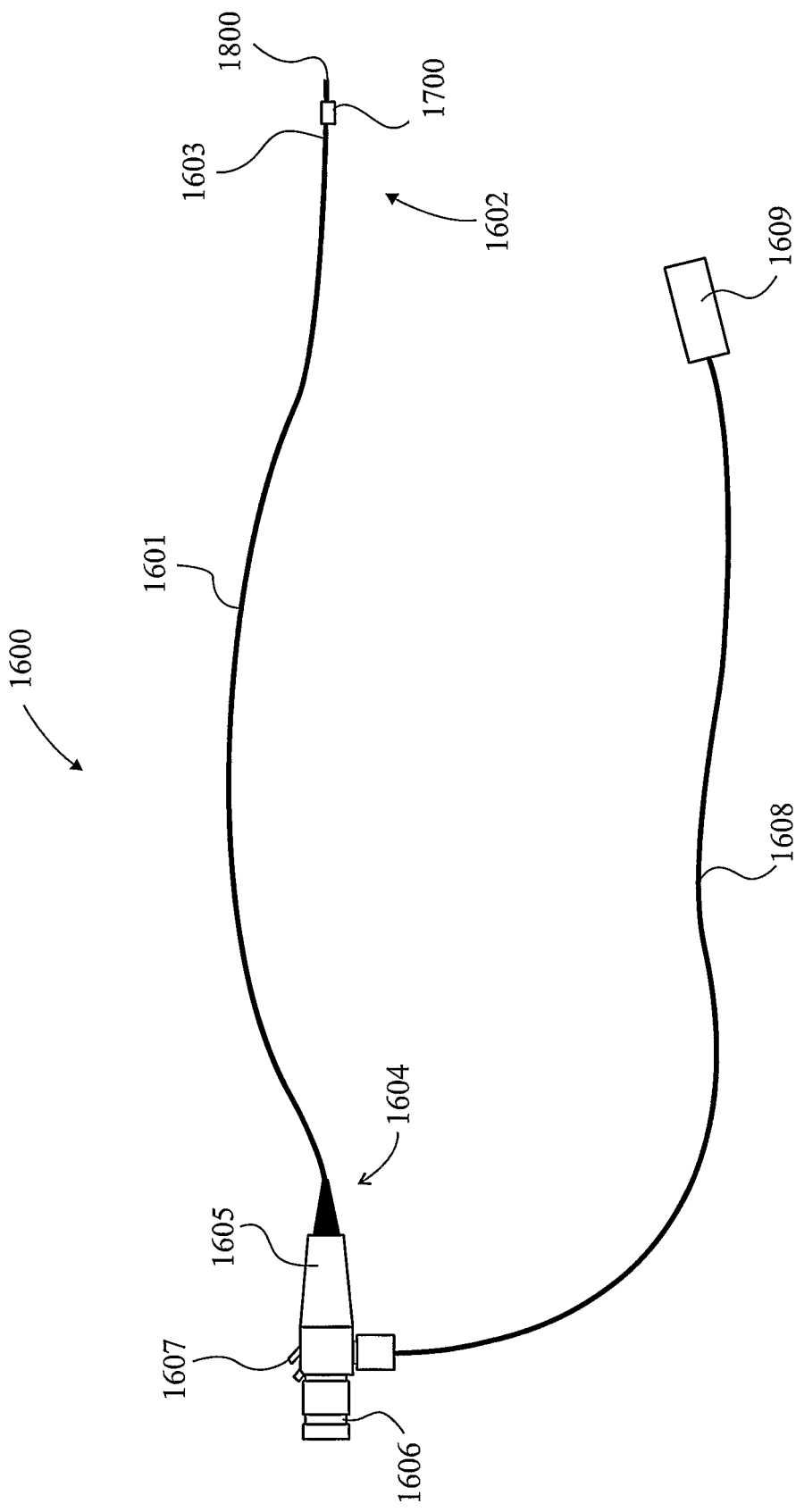
FIG. 16 illustrates how an embodiment of the present invention can be used to deliver medicaments.

FIG. 16 illustrates how the vapour explosion technology can be applied in accordance with a further embodiment of the present invention to provide a medical drug delivery apparatus and method or apparatus and method for clearing a blockage in a patient. FIG. 16 illustrates an endoscope 1600 which has a flexible and manoeuvrable shaft 1601 which may be located in an intestinal track or respiratory system or cardiovascular system portion of a human body. A distal end region 1602 of the flexible shaft 1601 includes a flexible tip 1603. The tip allows an end stop device 1700 (shown more clearly in FIG. 17) to be manoeuvred with respect to a patient's body and allows the end of the shaft to be positioned by a surgeon. A proximal end 1604 of the shaft 1601 terminates in an endoscope body portion 1605 which includes an eye piece 1606 and openings 1607 for auxiliary equipment. A further cable 1608 connects the endoscope body 1605 to an input connection 1609 which supplies any required light, air, water or other needed utility to the endoscope.

Figure 17:
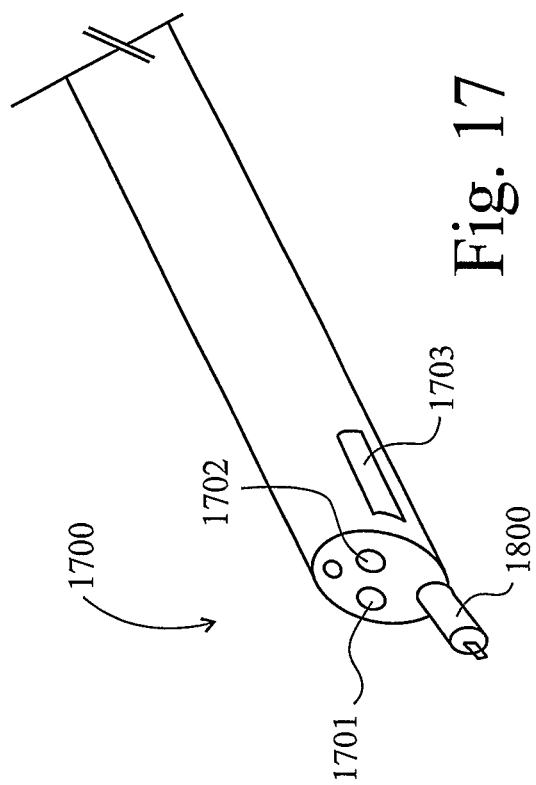
FIG. 17 illustrates an end of an endoscope.

As shown more clearly in FIG. 17, the end of the endoscope 1700 includes a light 1701 for illuminating a region surrounding the end of the endoscope for a surgeon and a camera 1702 for providing visual images of the region of the patient. The signals from the camera 1702 may be provided to the eye piece 1606 or outputting signals via the connection 1609 or via an opening 1607 so that images are displayed on a display, such as an LCD screen.

Figure 18:
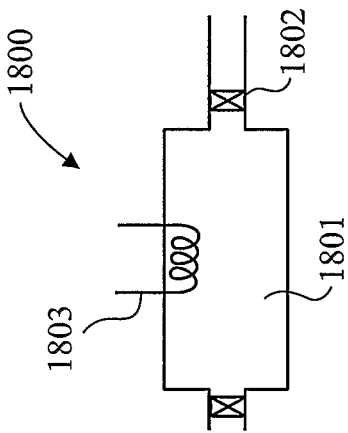
FIG. 18 illustrates how a medicament can be delivered.

The end 1700 of the endoscope 1600 also includes a medicament delivery chamber 1800 as seen more clearly in FIG. 18. Power and control signals are supplied to the medicament delivery chamber 1800 via controller 1703. The liquid vapour material ejected from the chamber 1801 may be used according to a number of methodologies. In one of these, the endoscope may be manoeuvred to a location where medicament is to be dispensed at a particular location. Liquid may then be input into the chamber 1801 (or may already be so inserted) by opening inlet valve 1802 and then a heater unit 1803 energised to raise the temperature and pressure of the liquid medicament. The medicament can then be dispensed when the pressure and/or temperature reaches a predetermined value ejecting vaporised medicament and liquid medicament at a desired location. As with all of the above-described embodiments, the ejection cycle may be repeated many times if desired.

As an alternative, the liquid and liquid vapour ejected material can be used to clear a blockage in arteries and/or veins or the like. In this sense embodiments of the present invention can be used in the bloodstream at blockages (such as in restricted blood flow disease due to furring of the arteries). In this case a water based or other neutral solution ejected by the above-mentioned techniques may be applied longitudinally along the line of a blocked vein/artery to thereby unblock the blockage. This is in addition to or replaces the present methodology which uses an expanding tube/balloon to clear the offending passage.

According to the embodiment of the present invention shown in FIG. 16, a camera operated by a doctor is attached to a nano vapour explosion device and used to put a drug in exactly the right spot where a malfunction has taken place. Embodiments of the present invention are not restricted to intestinal use but rather could be used also in a respiratory system of the main tracheal tubes and in the blood environment may have applications in the cardiovascular system.

Although the embodiment of the present invention described with respect to FIGS. 16 to 18 have been described relating to the use of endoscope-like devices, embodiments of the present invention are not so restricted. Rather, embodiments of the present invention can be used to deliver drugs at the desired locations by introducing a device in the form of a pill-like device which then moves on its own, for example through the bloodstream or the intestinal track and which is tracked by X-ray machinery with a dye and a scanning system so that an operator sees on the screen where the device has got to. A wireless signal may be then transmitted to the device in the human body when a doctor determines that the device is at a desired location. The device would then eject drug or merely liquid to either deliver medicament or open a blocked passage at a desired location.

A further application of the vapour explosion device of the present invention is as part of a respiratory drug delivery system. Respiratory drug delivery systems are used to deliver drugs directly to the respiratory system to treat numerous respiratory diseases such as asthma, cystic fibrosis, and chronic obstructive pulmonary disease (COPD). Additionally, in recent times it has been realised that the lungs can be used as a portal of entry for systematic drug therapy, for example, inhaled insulin has been successfully administered and is likely to become an alternative routine treatment to injecting insulin in the therapy of diabetes.

There are three main types of respiratory drug delivery systems, metered dose inhalers, dry powder inhalers and nebulizers. Pressurised metered dose inhalers release a metered volume or specific value of pressurised fluid into a patient's airways. On release the fluid evaporates rapidly leaving the drug in dry form suitable for inhalation. Dry powder inhalers contain a dry powder which is dislodged when the patient inhales air through the inhaler, the force of the inhalation then carries the dry powder into the patient's lungs. Both metered dose inhalers and dry powder inhalers will give out a predetermined amount of drug in one inhalation, the patient will take a certain amount of these doses during a day. A third type of respiratory drug delivery system is the nebulizer which converts medicine stored in liquid form into a gaseous suspension of medicine particles, such as an aerosol or mist. The patient will breathe in this mist and the drug is delivered into the respiratory system. There are two main types of nebulizer, jet nebulizers and ultrasonic nebulizers. Jet nebulizers work by applying pressurised gas through a narrow opening which creates a negative pressure upon a medicine reservoir, which draws particles of the drug solution from its reservoir forming a mist for the patient to inhale. Ultrasonic nebulizers use a rapidly vibrating piezoelectric crystal which forms a fountain of liquid from which the mist rises. Nebulizers slowly convert the liquid medicine into a mist over a period of about 15 minutes, during which time the user will be continually inhaling the medicine in mist form. Nebulizers deliver much stronger doses of medicine and are therefore usually used for patients with severe respiratory problems.

According to an embodiment of the present invention a vapour explosion device takes liquid from a reservoir and outputs a vapour mist. The reservoir contains a medicine and thus medicine can be administered in the form of mist suitable for inhalation. The explosion device emits vapour (or mist) in short sharp bursts, the volume of vapour released corresponding to the amount of liquid put into the vapour explosion chamber. Therefore, the device can be used to administer single units of medicine in a vapour form similar to a metered dose inhaler. A further feature of an embodiment of the present invention is that it can continually emit bursts of vapour in very quick succession. Therefore embodiments of the present invention can be used to administer medicine continually for a set period of time like a nebulizer. Furthermore, as the vapour explosion device can perform the function of both these types of respiratory drug delivery, a multi-functional system capable of delivering both single units of medicine vapour and continual bursts of medicine vapour may be provided.

The vapour explosion device based respiratory drug delivery system of the present invention is advantageous over prior art respiratory drug delivery systems in that it has a very long throw, a wide angle spray and the spray it creates has a very small drop size. The long throw and wide angle spray allows for the medicine to get further into the respiratory system and it is well spread out therefore more likely to be better carried by a patients inhalation. Furthermore, the small drop size provides better absorption of the medicine by the respiratory system. Drop sizes of 1-5 µm are ideal as larger ones often deposit proximal to the airways, while smaller particles have poor deposition and are largely exhaled.

Figure 19:
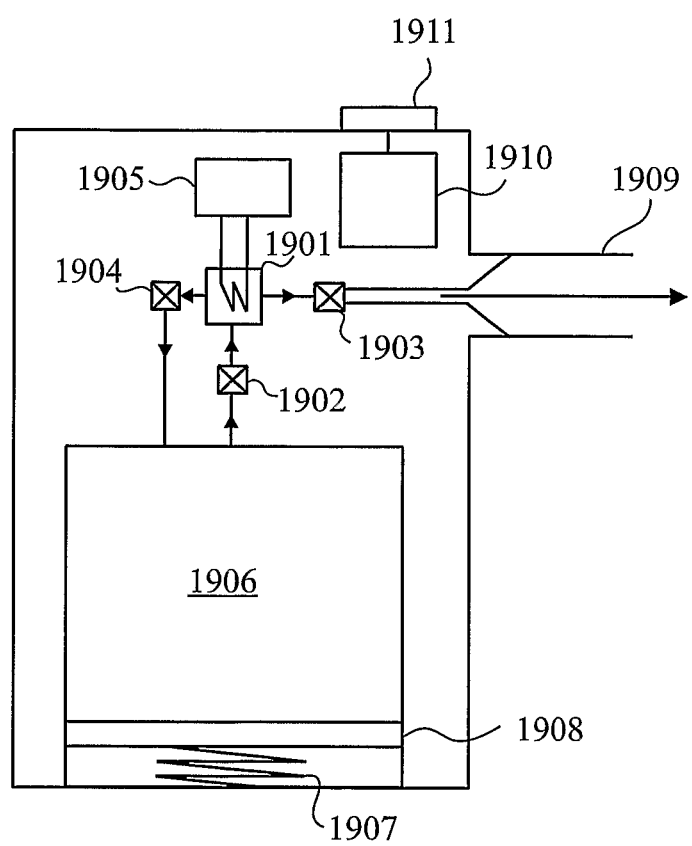
FIG. 19 illustrates how an embodiment of the present invention can be used as a portable nebulizer.

FIG. 19 illustrates how the vapour explosion device of the present invention could be embodied as a portable nebulizer. The portable nebulizer embodiment of the present invention comprises a vapour explosion chamber, with inlet valve 1902, exhaust valve 1903 and optional return valve 1904. The chamber is heated via a heating element powered by a battery 1905 or other such power source, and supplied with suitable fluid via a medicine reservoir 1906. The portable nebulizer could also be powered by a mains power supply as well as or instead of a battery. The reservoir 1906 can have a fixed amount of liquid within it, a spring 1907 and moving piston 1908 can be used to apply pressure to the reservoir 1906 to enable fast refill of the vapour explosion chamber 1901. Alternatively, medicine can be stored in a pre-pressurised storage device which may be detachable from the nebulizer, allowing for easy replenishment of medicine by replacement of the storage device. The liquid within the reservoir may be pure medicine or medicine suspended within a carrier liquid. A user control interface 1911 allows the user to control the nebulizer, a control circuit 1910 may then process input signals from the user control interface and control the nebulizer responsively.

The process of vaporising the medicine in accordance with the portable nebulizer of FIG. 19 starts by passing medicine from the medicine reservoir 1906 through the inlet valve 1902, filling up the chamber 1901. When a predetermined amount of medicine is within the chamber, all valves will be closed and the heater will heat up the chamber until a trigger temperature and pressure are reached to enable the exhaust valve to open. The exhaust valve then opens and a vapour or mist is emitted along mouthpiece 1909. The distance between the outlet valve 1903 and the end of the mouthpiece is made sufficiently long for the mist to cool before it reaches the end of the mouthpiece and the patient then inhales the drug. This ejection process would then be repeated at a specific frequency, either for a predetermined period of time or until a predetermined amount of medicine has been vaporised. The size of the chamber 1901 or the amount of liquid put into the chamber will correlate to the amount of liquid required to be emitted by each burst of spray.

Figure 20:
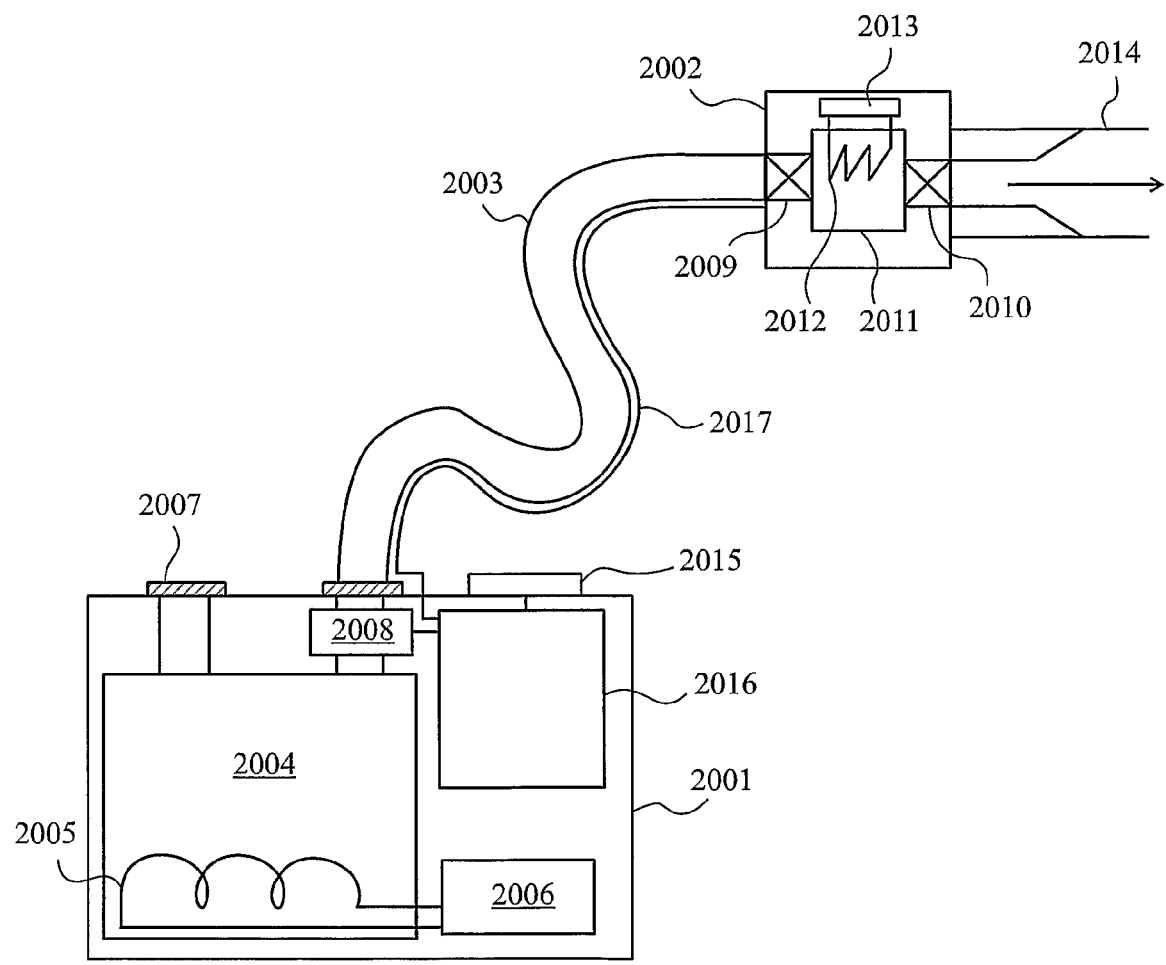
FIG. 20 illustrates how the chambers of the various described embodiments may be shaped.

FIG. 20 shows a desktop nebulizer which comprises three main constituent parts, a nebulizer main body 2001, a vapour explosion device 2002 and a medicine transportation pipe 2003 which connects the first two constituent parts together. The nebulizer main body includes a medicine reservoir 2004 which can contain a heating element 2005 to keep the medicine at a temperature close to but below a temperature required by the vapour explosion device, the heating element is powered by a power source 2006. The reservoir has a reservoir inlet to allow for refilling of medicine to the reservoir, and a reservoir pump 2008 to pump medicine out of the reservoir. The pump provides pressurised medicine to the medicine transportation pipe 2003 to enable fast refilling of the vapour explosion device. The vapour explosion device as shown in FIG. 20 works in accordance with previous embodiments of the vapour explosion device, with inlet valve 2009, exhaust valve 2010, vapour explosion chamber 2011, heater 2012 and heater power source 2013, with medicine being released in vapour form from a mouthpiece 2014. A return port and valve could be incorporated within the present embodiment to help refill the chamber faster. A user control interface can be mounted on the nebulizer main body 2001 to allow for the user to control the nebulizer. A control circuit 2016 is shown within the nebulizer main body for the purpose of processing input signals from the user control interface 2015 and controlling the nebulizer responsively. A control line 2017 can be placed parallel to the medicine transportation pipe 2003 to connect the control circuit 2016 to the vapour explosion device. It is worth noting that the heater power source 2013 could be a battery or mains power supply supplied via a power line from the nebulizer main body.

FIG. 20 shows the medicine reservoir 2004 as a refillable reservoir. In this embodiment the amount of medicine required by the patient could be placed in the reservoir and then the nebulizer could run until all has been ejected. Alternatively the reservoir could be filled to the maximum and then the nebulizer could emit a predetermined amount of medicine. It should be understood that a refillable reservoir is not necessary according to embodiments of the present invention and a pre-packed container of medicine could alternatively be used. Furthermore, a pressurised container could be used, thus not requiring a pump.

Figure 21:
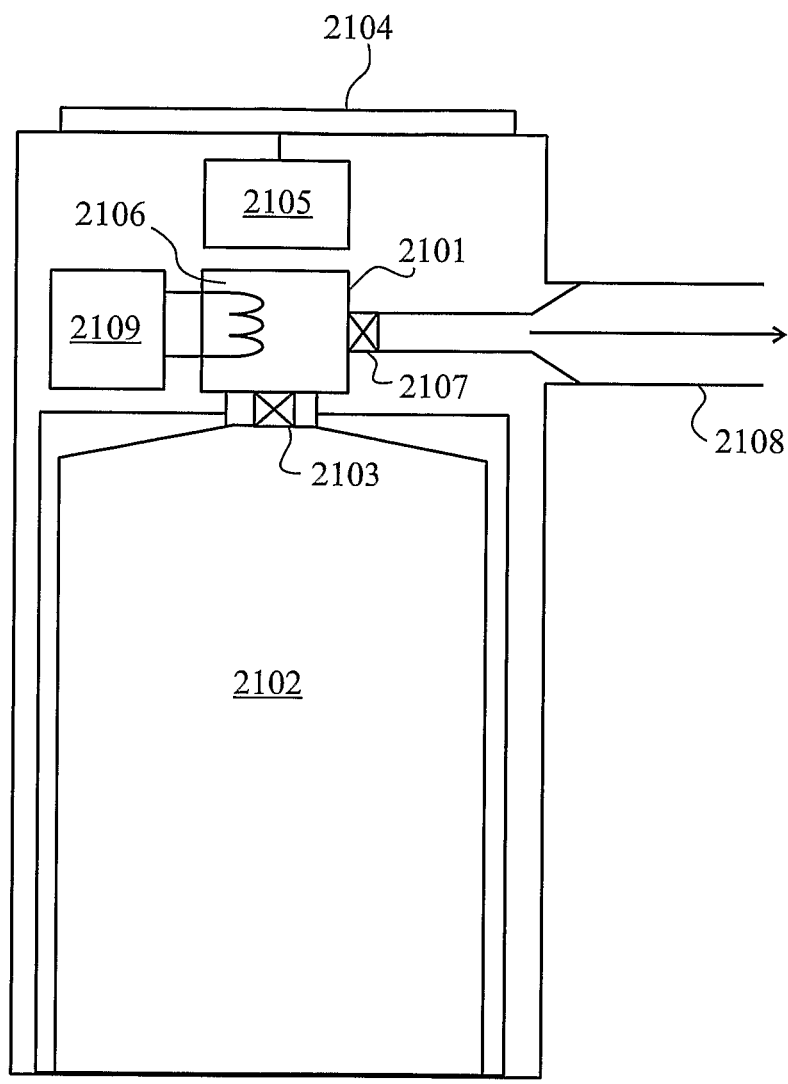

FIG. 21 shows a metered dose inhaler according to an embodiment of the present invention. This embodiment of the present invention shows a vapour explosion chamber 2101 which receives medicine from a medicine reservoir 2102 through an inlet valve 2103. The amount of medicine within the vapour explosion chamber corresponds to the dose required by the user. When a user presses the control button 2104, a control circuit 2105 controls a heating element 2106 along with the inlet valve 2103 and exhaust valve 2107 to emit medicine in vapour form through the mouthpiece 2108 for the user to inhale. The heating element 2106 is powered by a power source 2109 which may be a battery or a connection to a mains power supply. The medicine reservoir 2102 in FIG. 21 is shown as a pressurised container for providing pressurised liquid to the inlet valve 2103 to enable fast refilling of the vapour explosion chamber 2101. It is should be understood that refillable medicine reservoirs could alternatively be used, as could unpressurised containers. A return port is not shown in FIG. 21 but could also be incorporated.

It will be appreciated that embodiments of the present invention may also be utilised to provide a needleless injector.

In all applications of the vapour explosion device used as part of a respiratory drug delivery system the patient can receive the drug either through a mouth piece which would sit inside the mouth or a face mask which would sit on the face over the mouth and/or nose. The medicine could also be delivered directly into any other part of a patient's respiratory system.

For all respiratory drug delivery applications the trigger temperature for the chamber 1901 needs to be above the boiling point of the liquid or liquids within the chamber to ensure maximum explosion of liquid from the chamber. The trigger temperature is recommended to be approximately 20-30° C. above the boiling point of the liquid within the chamber with the highest boiling point to ensure that a very fine spray best suited to this application is produced. The trigger pressure can be as low as 4-6 bars although the device would work at other pressures. The diameter of the exhaust nozzle may be best suited to this application if within the range of 0.05-0.5 mm.

To maximise the delivery of medicine and minimise the waste of medicine in a vapour explosion device based nebulizer a breath actuated delivery system could be incorporated in which an electronic detection system or mechanical valve system is used to determine when the user is inhaling, and then only emit medicine when the user inhales so that medicine is not wasted during exhalation. Such functionality can be achieved manually but many people find it difficult to coordinate their breathing with the switching of the nebulizer. It is worth noting that, such sensing could also be used in a metered dose system, as people often find it difficult coordinating the ejection of medicine with inhalation.

It will be appreciated that the heating element by which liquid is raised above its saturation point in the ejection chamber may be chemical in nature. That is to say two components may be provided which, when combined, provide an exothermic reaction generating sufficient quantity of heat so as to 'boil' the liquid. A user would activate the two components just before use and then wait until discharge was ready. This could be identified in a number of ways such as a user display illuminating or making a noise, material being visibly ejected or a predetermined time elapsing.

Although embodiments of the present invention described with respect to FIGS. 19 to 21 have been described relating to particular respiratory drug delivery systems, embodiments of the present invention are not so restricted.

Figure 22:
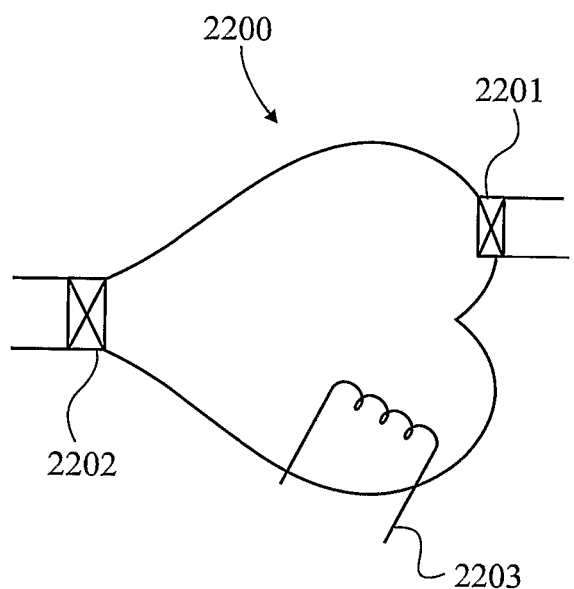

FIG. 22 illustrates a liquid and liquid vapour explosion chamber 2200 which may be utilised according to any of the above-described embodiments. It will be understood that embodiments of the present invention are not restricted to use with substantially cylindrical shaped ejection chambers. Rather, unusual shapes or spherical shapes or, as in the case of FIG. 22, heart-shaped chambers having an inlet valve 2201, exit valve 2202 and heater element 2203 may be utilised.

Embodiments of the present invention provide fundamental core technology relating to the use of an ejection chamber which ejects target matter via a vapour explosion process. By ejecting material via an explosive process the distance traversed by the spray of liquid and liquid vapour is greatly increased relative to known ejection systems. Also ejection occurs very rapidly and with a small chamber in the order of tens of microseconds.

According to embodiments of the present invention, pressure in a chamber is increased by heating liquid in it. The liquid expands due to thermal expansion and therefore provides a higher pressure. Heating is achieved by electrical heating element or by other means such as via heat exchangers transferring heat from a local heat source into the liquid. All of the embodiments of the present invention described above can be modified so that instead of heating liquid in an ejection chamber, pre-heated liquid is supplied at an inlet to the chamber under high pressure. Pressure would be built up in the chamber by continuing to pump pre-heated liquid into the chamber. This could be achieved via an external pump able to pump at high pressure. At some predetermined pressure value above a pressure into which ejected material is to be ejected, the inlet valve would be closed and an exit valve opened. The instantaneous reduction in pressure would be calculated to instigate a vaporization process of the liquid by virtue of its elevated temperature with respect to its boiling temperature. Liquid and vapour would thus literally explode from the exit valve of the chamber.

In the case of using water as a working liquid, velocities of up to 20 meters per second from a chamber just under 1 mm in size with a chamber pressure of 1.1 bar and injecting into ambient for example atmospheric pressure (1.0 bar) can be achieved. In the case of a hydrocarbon liquid fuel being used, velocities of up to 100 meters per second can be achieved from a chamber about 2 cms in size and under a pressure of 10 bar injecting into a combustion chamber at 6 bar (in other words a 1 bar pressure difference between the ejection chamber and an adjacent combustion chamber).

Inlet and exit valves can be electronically controlled based on the pressure in the various vessels which can be easily monitored/measured via one or more sensors such as pressure transducers. When a certain pressure in the vessel is reached, the exit valve will open and when it falls below a second certain value the valve is closed. For the inlet valve this can either be opened and closed when certain higher limit and lower limit pressures are reached in the chamber or could open and close in a reverse fashion with respect to the exit valve. That is to say, when the exit valve is opened the inlet valve would be controlled to close and when the exit valve closes the inlet valve would open.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. Apparatus for injecting fuel into a combustion zone, comprising:
   an ejection chamber to hold a portion of a liquid fuel;
   an inlet valve arranged to selectively open to transfer liquid fuel into the ejection chamber and then to selectively close to seal the portion of the liquid fuel in the ejection chamber;
   an exit valve arranged to selectively open to eject fuel from said ejection chamber through the exit valve in a vapor explosion process, then through a neck region when a parameter associated with said ejection chamber satisfies a predetermined condition such that opening of the exit valve causes liquid fuel in the ejection chamber to boil rapidly within the ejection chamber, the neck region being narrower in cross-sectional diameter than the ejection chamber;
   at least one pressure or temperature sensor that generates one or more signals for determining pressure in the ejection chamber; and
   an electronic controller for electronically controlling the inlet valve and the exit valve to selectively open and close based on the pressure in the ejection chamber determined from the one or more signals received from the at least one pressure or temperature sensor;
   wherein liquid fuel and/or liquid vapor are ejected from the ejection chamber into the combustion zone via the exit valve thereby injecting fuel into the combustion zone,
   and wherein said exit valve is arranged to open when a temperature of the liquid fuel in the ejection chamber is above a boiling point temperature associated with the liquid fuel at a downstream position from the exit valve,
   and wherein the parameter is the temperature of the liquid fuel in the ejection chamber and the predetermined condition is the temperature of the liquid fuel being above said boiling point temperature.

2. The apparatus as claimed in claim 1, further comprising: a heater element disposed in said ejection chamber or proximate to said ejection chamber for raising a temperature of the liquid fuel in said chamber.

3. The apparatus as claimed in claim 1, in combination with a pump member, the pump member disposed in said ejection chamber or proximate to said ejection chamber for raising a pressure of the liquid fuel in said ejection chamber.

4. The apparatus as claimed in claim 1 wherein said exit valve is located in said combustion zone.

5. The apparatus as claimed in claim 1, further comprising: a storage chamber arranged to store liquid fuel; wherein said inlet valve is arranged to selectively transfer a portion of liquid fuel from said storage chamber into said ejection chamber.

6. The apparatus as claimed in claim 5, further comprising:
a further heating member arranged to heat liquid fuel in said storage chamber prior to transfer into said ejection chamber.

7. The apparatus as claimed in claim 5, further comprising:
an inlet pipe connecting the storage chamber to the inlet valve, the inlet pipe being arranged proximate to said combustion zone or having a heat exchanger between hot parts of the engine and the inlet pipe to thereby heat fuel transferring from the storage chamber to the ejection chamber.

8. The apparatus as claimed in claim 1, further comprising:
said liquid fuel comprises a multi-component fuel and said exit valve is arranged to open when a temperature of the liquid fuel is equal to or greater than a saturation temperature associated with a selected one of said multiple components.

9. The apparatus as claimed in claim 8 wherein said selected one component comprises a lightest component of said multi-component fuel.

10. The apparatus as claimed in claim 8 wherein said selected one component comprises a heaviest component of said multi-component fuel.

11. The apparatus as claimed in claim 1, further comprising:
said ejection chamber is located proximate to said combustion zone and is arranged to absorb heat generated by combustion of fuel in the combustion zone.

12. The apparatus as claimed in claim 11, further comprising:
a heat exchanger arranged to transfer heat from said combustion zone to said ejection chamber.

13. The apparatus as claimed in claim 1, wherein the liquid vapor and/or liquid fuel are ejected as a spray having a throw greater than 20.

14. The apparatus as claimed in any claim 1, wherein said liquid vapor and/or liquid fuel are ejected as a spray having a throw greater than 100.

15. The apparatus as claimed in claim 1, wherein said liquid fuel comprises kerosene or petrol or diesel fuel.

16. The apparatus as claimed in claim 1, wherein said ejection chamber is manufactured from a metallic material.

17. The apparatus as claimed in claim 1, further comprising at least one power source.

18. The apparatus as claimed in claim 1, wherein said ejection chamber is substantially cylindrical in shape and the neck region is at an exit end thereof, the exit valve being located at the neck region.

19. The apparatus as claimed in claim 18 wherein said neck region includes a narrow ejection orifice via which liquid fuel and liquid vapor is ejected into the combustion zone.

20. The apparatus as claimed in claim 19 wherein a cross section of the ejection orifice has a diameter less than a cross section of the neck region.

21. The apparatus as claimed in claim 1, further comprising:
an ignition source located in the combustion zone for igniting the liquid vapor and/or liquid fuel ejected into the combustion zone.

22. A method for injecting fuel into a combustion zone, comprising the steps of:
providing an ejection chamber arranged to hold a portion of a liquid fuel;
selectively opening an inlet valve to transfer a portion of liquid fuel into the ejection chamber;
selectively closing the inlet valve to seal a portion of the liquid fuel in the ejection chamber;
heating the liquid fuel in the ejection chamber to a temperature above a boiling point temperature associated with said liquid fuel at a downstream position from an exit valve;
monitoring pressure in the ejection chamber via at least one pressure or temperature sensor;
controlling the inlet and exit valves based on the pressure in said ejection chamber;
selectively opening the exit valve of said ejection chamber when a parameter associated with said ejection chamber satisfies a predetermined condition such that opening of the exit valve causes liquid fuel in the ejection chamber to boil rapidly within the ejection chamber; and
ejecting liquid vapor and/or liquid fuel via a vapor explosion process from the ejection chamber into the combustion zone via the exit valve and then through a neck region narrower in cross-sectional diameter than the ejection chamber,
wherein the parameter is the temperature of the liquid fuel in the ejection chamber and the predetermined condition is the temperature of the liquid fuel being above said boiling point temperature.

23. The method as claimed in claim 22, further comprising the steps of: heating liquid fuel to thereby increase a temperature of liquid fuel held in the ejection chamber via a heating element disposed in or proximate to the ejection chamber.

24. The method as claimed in claim 23, further comprising the steps of:
heating liquid fuel in the ejection chamber prior to the step of opening the exit valve.

25. The method as claimed in claim 22, further comprising the steps of: increasing pressure in the ejection chamber via a pump member disposed in or proximate to said ejection chamber.

26. The method as claimed in claim 22, further comprising the steps of:
determining when the parameter satisfies said predetermined condition and opening the exit valve responsive to said determination.

27. The method as claimed in claim 22, further comprising the steps of:
preheating liquid fuel supplied to the inlet valve prior to entry of the liquid fuel into the ejection chamber.

28. The method as claimed in claim 22, further comprising the steps of:
monitoring pressure and/or temperature in the ejection chamber via at least one sensor.

29. The method as claimed in claim 22, further comprising the steps of:
heating the liquid fuel in the ejection chamber to a temperature substantially equal to or above a saturation temperature associated with the liquid fuel at a pressure equal to a pressure at a location downstream of said exit valve.

\* \* \* \* \*